United States Patent
Kawamura

(10) Patent No.: US 11,089,967 B2
(45) Date of Patent: Aug. 17, 2021

(54) VALVE, FLUID CONTROLLER, AND SPHYGMOMANOMETER

(71) Applicant: Murata Manufacturing Co., Ltd., Kyoto (JP)

(72) Inventor: Kenichiro Kawamura, Kyoto (JP)

(73) Assignee: MURATA MANUFACTURING CO., LTD., Kyoto (JP)

(*) Notice: Subject to any disclaimer, the term of this patent is extended or adjusted under 35 U.S.C. 154(b) by 491 days.

(21) Appl. No.: 16/156,273

(22) Filed: Oct. 10, 2018

(65) Prior Publication Data

US 2019/0038145 A1 Feb. 7, 2019

Related U.S. Application Data

(63) Continuation of application No. PCT/JP2017/011579, filed on Mar. 23, 2017.

(30) Foreign Application Priority Data

May 9, 2016 (JP) .............................. JP2016-093612

(51) Int. Cl.
*A61B 5/0404* (2006.01)
*A61B 5/0235* (2006.01)
(Continued)

(52) U.S. Cl.
CPC .......... *A61B 5/0235* (2013.01); *G05D 7/0113* (2013.01); *G05D 16/163* (2013.01);
(Continued)

(58) Field of Classification Search
CPC .... A61B 5/0235; A61B 5/022; G05D 7/0113; G05D 16/163; A61M 39/24;
(Continued)

(56) References Cited

U.S. PATENT DOCUMENTS

2012/0316492 A1* 12/2012 Chappel .............. F16K 99/0057 604/67
2013/0178752 A1* 7/2013 Kodama ............... F16K 15/145 600/498

(Continued)

FOREIGN PATENT DOCUMENTS

| CN | 104246228 A | 12/2014 |
| JP | S60-027902 U | 2/1985 |

(Continued)

OTHER PUBLICATIONS

International Search Report for International Application No. PCT/JP2017/011579 dated May 30, 2017.
(Continued)

*Primary Examiner* — Minh Q Le
(74) *Attorney, Agent, or Firm* — Pearne & Gordon LLP

(57) ABSTRACT

A fluid controller includes a piezoelectric pump, a valve, and a cuff. The valve includes a first valve housing, a diaphragm, and a second valve housing. The second valve housing has a second air hole, a third air hole, and a first valve seat. The second air hole connects to the internal space of the cuff. The third air hole connects to the outside of the fluid controller. The first valve seat is formed around the third air hole. Together, the second valve housing and the diaphragm form a first flow passage. The first flow passage connects the second air hole and the third air hole to each other. The second valve housing has a protruded portion protruding toward the diaphragm and providing a portion of the first flow passage. The shortest distance between the protruded portion and the diaphragm is less than the diameter of the third air hole.

20 Claims, 18 Drawing Sheets

(51) Int. Cl.
*G05D 7/01* (2006.01)
*G05D 16/16* (2006.01)
*A61M 39/24* (2006.01)
*A61B 5/022* (2006.01)
*F04B 43/04* (2006.01)
*F04B 53/10* (2006.01)
*F16K 7/17* (2006.01)
*F16K 11/22* (2006.01)
*F16K 31/128* (2006.01)

(52) U.S. Cl.
CPC .............. *A61B 5/022* (2013.01); *A61M 39/24* (2013.01); *A61M 2039/2493* (2013.01); *F04B 43/043* (2013.01); *F04B 53/106* (2013.01); *F16K 7/17* (2013.01); *F16K 11/22* (2013.01); *F16K 31/128* (2013.01)

(58) Field of Classification Search
CPC .. A61M 2039/2493; A61M 2039/2413; A61M 2039/2406; F16K 7/17; F16K 11/22; F16K 11/105; F16K 31/128; F16K 31/1266; F04B 53/106; F04B 43/043
USPC ............ 600/498; 137/102, 315.05, 503, 843, 137/625.12; 251/331
See application file for complete search history.

(56) References Cited

U.S. PATENT DOCUMENTS

| | | |
|---|---|---|
| 2013/0331715 A1 | 12/2013 | Sano |
| 2015/0034847 A1 | 2/2015 | Kotani et al. |
| 2015/0150470 A1* | 6/2015 | Sano .................... F04B 43/046 600/498 |
| 2016/0076537 A1 | 3/2016 | Kawamura et al. |
| 2016/0327031 A1* | 11/2016 | Ito .......................... F04B 45/04 |
| 2017/0072117 A1* | 3/2017 | Kurihara .............. A61M 1/0001 |
| 2017/0215744 A1 | 8/2017 | Kawamura |
| 2017/0292509 A1* | 10/2017 | Kurihara ............... F04B 43/046 |
| 2018/0079088 A1* | 3/2018 | Takeuchi ................. F16K 7/17 |
| 2018/0202562 A1 | 7/2018 | Kotani et al. |
| 2018/0368704 A1* | 12/2018 | Kawamura .......... A61B 5/0225 |
| 2020/0217426 A1* | 7/2020 | Kawamura ............. F04B 45/04 |
| 2020/0355278 A1* | 11/2020 | Kawamura ............... F16K 7/17 |

FOREIGN PATENT DOCUMENTS

| | | |
|---|---|---|
| JP | 2012-217682 A | 11/2012 |
| WO | 2013/157304 A1 | 10/2013 |
| WO | 2016/063710 A1 | 4/2016 |

OTHER PUBLICATIONS

Written Opinion for International Application No. PCT/JP2017/011579 dated May 30, 2017.

* cited by examiner

VALVE, FLUID CONTROLLER, AND SPHYGMOMANOMETER

This is a continuation of International Application No. PCT/JP2017/011579 filed on Mar. 23, 2017 which claims priority from Japanese Patent Application No. 2016-093612 filed on May 9, 2016. The contents of these applications are incorporated herein by reference in their entireties.

DESCRIPTION OF THE RELATED ART

The present disclosure relates to a valve for suppressing the reverse flow of a fluid, a fluid controller including the valve, and a sphygmomanometer including the fluid controller.

DESCRIPTION OF THE RELATED ART

Patent Document 1 discloses a fluid controller including a valve.

FIG. 14 is a cross-sectional view of the components of a fluid controller 900 according to Patent Document 1. The fluid controller 900 includes a piezoelectric pump 10, a valve 901, and a cuff 109. The fluid controller 900 is included in a sphygmomanometer. The piezoelectric pump 10 will be described later in detail. The valve 901 includes a first valve housing 991, a diaphragm 920, and a second valve housing 992.

The first valve housing 991 has a first air hole 910, a first air hole 911, and a valve seat 938. The first air hole 910 connects to a discharge hole 56 in the piezoelectric pump 10. The first air hole 911 connects to a discharge hole 55 in the piezoelectric pump 10. The valve seat 938 protrudes toward the diaphragm 920. The second valve housing 992 has a second air hole 912, a third air hole 913, and a valve seat 939. The second air hole 912 connects to the cuff 109. The third air hole 913 is open to the atmosphere. The valve seat 939 is formed around the third air hole 913.

The diaphragm 920 has an opening 921 in a center portion of a portion opposite to the valve seat 938. Together, the diaphragm 920, the first valve housing 991, and the second valve housing 992 form a first valve chamber 931 and a second valve chamber 933. The first valve chamber 931 connects to the first air hole 910 and the first air hole 911. The second valve chamber 933 connects to the second air hole 912.

The operation of the fluid controller 900 when blood pressure is measured will next be described.

FIG. 15 is a diagram for explaining the flow of the air in the fluid controller 900 during driving of the piezoelectric pump 10 shown in FIG. 14. FIG. 16 is a diagram for explaining the flow of the air in the fluid controller 900 immediately after the piezoelectric pump 10 shown in FIG. 14 stops driving.

When the fluid controller 900 starts measuring blood pressure, the piezoelectric pump 10 discharges air to the first valve chamber 931 in the valve 901 through the discharge hole 55 and through the discharge hole 56. Thus, the pressure in the first valve chamber 931 exceeds the pressure in the second valve chamber 933. As shown in FIG. 15, the diaphragm 920 blocks the third air hole 913. The periphery of the opening 921 in the diaphragm 920 moves away from the valve seat 938. Accordingly, the air is carried from the piezoelectric pump 10 to the cuff 109 through the first air hole 911, the opening 921, and the second air hole 912 in the valve 901, thereby increasing the internal pressure of the cuff 109.

Next, when finishing measuring of blood pressure, the fluid controller 900 stops the driving of the piezoelectric pump 10. This enables the air in the pump chamber 45 and the air in the first valve chamber 931 to be rapidly discharged to the atmosphere through a suction hole 52 in the piezoelectric pump 10 and through the opening 921. Thus, the pressure in the first valve chamber 931 falls below the pressure in the second valve chamber 933. As shown in FIG. 16, the diaphragm 920 comes into contact with the valve seat 938, thereby blocking the opening 921. The diaphragm 920 moves away from the valve seat 939, such that the third air hole 913 is no longer blocked. Accordingly, the air in the cuff 109 is rapidly discharged through the third air hole 913 after flowing through the second air hole 912, a connecting passage 135, and the second valve chamber 933.

As such, after charging the compressed air into the cuff 109, the valve 901 can rapidly discharge the air from the cuff 109. Thus, the cuff 109 rapidly deflates, which enables the next measurement of blood pressure to be started immediately.

Patent Document 1: International Publication No. WO2013/157304

BRIEF SUMMARY OF THE DISCLOSURE

However, while the fluid controller 900 is charging the compressed air into the cuff 109 and discharging the compressed air from the cuff 109, there is a possibility of foreign matter F being contained in the cuff 109, as shown in FIG. 16. The foreign matter F is, for example, fibers of the cuff 109 that have peeled off from the inner surface of the cuff 109.

When the fluid controller 900 discharges the compressed air from the cuff 109, the foreign matter F flows through the second air hole 912 to the second valve chamber 933. Here, the foreign matter F should preferably be discharged through the third air hole 913 to the outside of the fluid controller 900. However, there are some possibilities, described below.

If the foreign matter F blocks the opening 921 or is stuck between the diaphragm 920 and the valve seat 939 as shown in FIG. 17, the fluid controller 900 will not be able to charge the compressed air into the cuff 109. Also, if the foreign matter F is stuck between the diaphragm 920 and the second valve housing 992, the flow rate of the air to be charged into the cuff 109 decreases. Meanwhile, if the foreign matter F clogs the third air hole 913 as shown in FIG. 18, the fluid controller 900 will not be able to discharge the compressed air from the cuff 109.

Accordingly, conventional valves, such as the valve 901, have the problem of causing a malfunction due to foreign matter.

An objective of the present disclosure is to provide a valve, a fluid controller, and a sphygmomanometer that are able to suppress a malfunction due to foreign matter from occurring.

A valve in the present disclosure includes a valve housing and a valve body. The valve housing has a first air hole, a second air hole, a third air hole, and a first valve seat formed around the third air hole. Together, the valve body and the valve housing form a first flow passage. The first flow passage connects the second air hole and the third air hole to each other. The valve body comes into contact with or moves away from the first valve seat.

The valve housing has a protruded portion that protrudes toward the valve body. The protruded portion forms a portion of the first flow passage. The first flow passage has a narrow portion formed by the protruded portion and the valve body. The shortest distance between the protruded portion and the valve body in the narrow portion is less than the minimum width of the third air hole.

For this configuration, for instance, the first air hole connects to a discharge hole in a pump, the second air hole connects to a container, and the third air hole is open to the atmosphere.

For this configuration, when the pump starts driving, gas flows through the discharge hole in the pump and then through the first air hole to the inside of the valve housing. Here, when the valve body comes into contact with the first valve seat, thereby blocking the third air hole, the gas that has flowed into the valve housing flows through the second air hole into the container. In this way, the compressed gas is charged into the container.

Subsequently, when the pump stops driving, the valve body moves away from the first valve seat, such that the third air hole is no longer blocked. Then, the compressed gas charged into the container flows through the second air hole to the first flow passage inside the valve housing. The gas that has flowed into the first flow passage is discharged through the third air hole to the outside of the valve housing.

For this configuration, when the compressed gas is discharged from the container, if the width of foreign matter that has flowed through the second air hole to the first flow passage is more than the diameter of the third air hole, the foreign matter cannot pass through the narrow portion.

Accordingly, even if the container contains foreign matter, the valve in the present disclosure can suppress a malfunction due to the foreign matter from occurring.

A fluid controller in the present disclosure includes: a pump having a discharge hole; a valve; and a container for storing gas. A first air hole in the valve connects to the discharge hole in the pump, and a second air hole in the valve connects to the container.

The fluid controller in the present disclosure has the valve in the present disclosure. Thus, the fluid controller in the present disclosure can also provide effects similar to those provided by the valve in the present disclosure.

Moreover, a sphygmomanometer in the present disclosure includes the fluid controller in the present disclosure.

Since the sphygmomanometer in the present disclosure includes the fluid controller in the present disclosure, the sphygmomanometer in the present disclosure can also provide effects similar to those provided by the fluid controller in the present disclosure.

The present disclosure can suppress a malfunction due to foreign matter from occurring.

DETAILED DESCRIPTION OF THE DISCLOSURE

Hereinafter, a fluid controller 100 according to Embodiment 1 of the present disclosure will be described.

Figure 1:
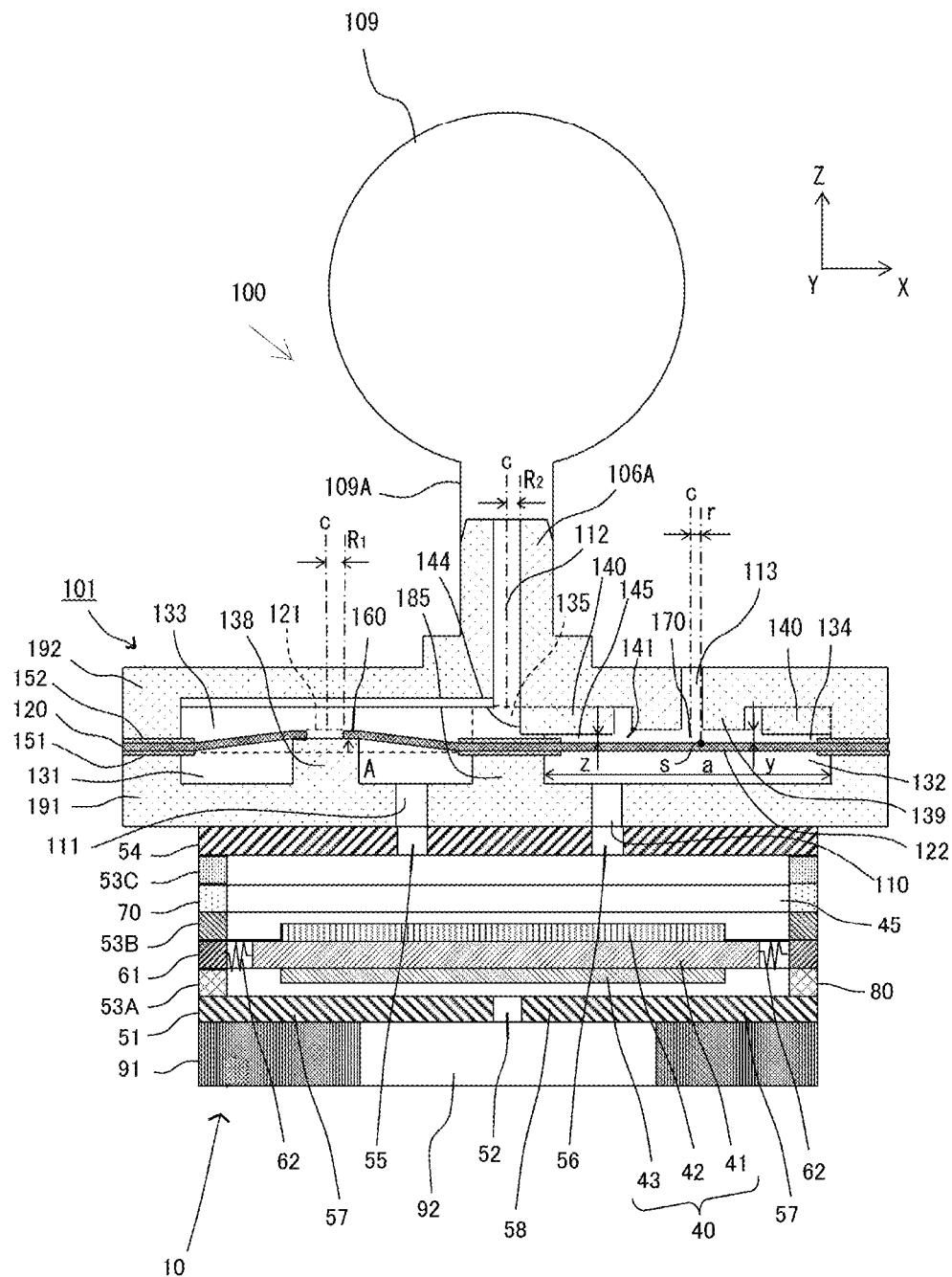
FIG. 1 is a cross-sectional view of the components of a fluid controller 100 according to Embodiment 1 of the present disclosure.

FIG. 1 is a cross-sectional view of the components of the fluid controller 100 according to Embodiment 1 of the present disclosure. The fluid controller 100 includes a piezoelectric pump 10, a valve 101, and a cuff 109. The fluid controller 100 is included in a sphygmomanometer that measures the blood pressure of a patient. The top surface of the piezoelectric pump 10 is joined to the bottom surface of the valve 101. Thus, the valve 101 is connected to piezoelectric pump 10.

The valve 101 has a nozzle 106A. A cuff rubber tube 109A of the cuff 109 is attached to the nozzle 106A of the valve 101. The cuff 109 is a flexible container capable of storing air.

It should be noted that the cuff 109 corresponds to an example of the container in the present disclosure.

Hereinafter, the configuration of the piezoelectric pump 10 and the configuration of the valve 101 will be described in detail. First, the configuration of the piezoelectric pump 10 will be described with reference to FIGS. 1 and 2.

Figure 2:
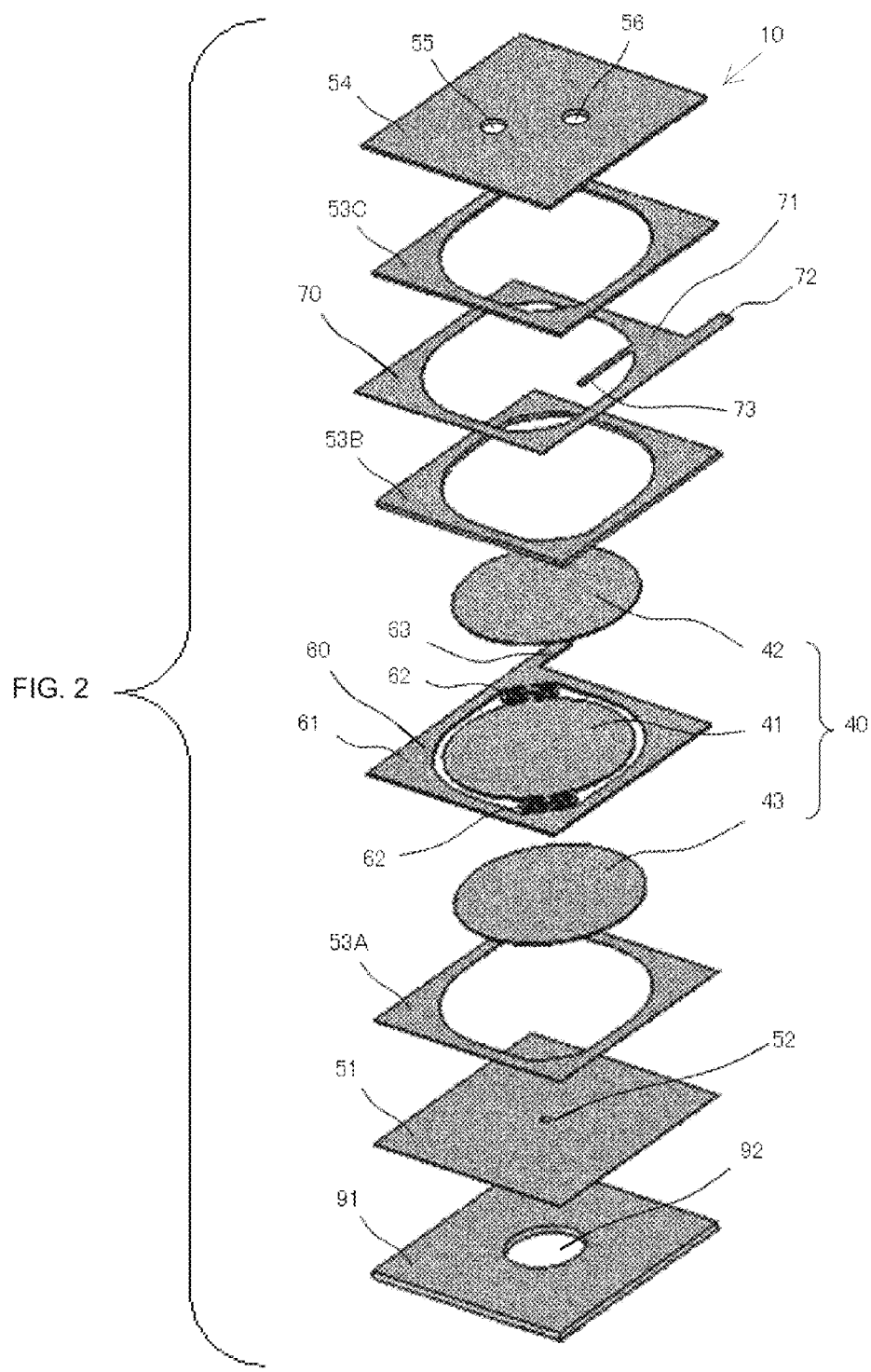
FIG. 2 is an exploded perspective view of a piezoelectric pump 10 shown in FIG. 1.

FIG. 2 is an exploded perspective view of the piezoelectric pump 10 shown in FIG. 1. The piezoelectric pump 10 includes a substrate 91, a flexible plate 51, a spacer 53A, a reinforcing plate 43, a vibration plate unit 60, a piezoelectric element 42, a spacer 53B, an electrode conducting plate 70, a spacer 53C, and a cover plate 54. These components of the piezoelectric pump 10 are sequentially stacked. A pump housing 80 is made up of the substrate 91, the flexible plate 51, the spacer 53A, a part of the vibration plate unit 60, the spacer 53B, the electrode conducting plate 70, the spacer 53C, and the cover plate 54. An internal space of the pump housing 80 corresponds to a pump chamber 45.

The vibration plate unit 60 has a vibration plate 41, a frame plate 61, connecting portions 62, and an external terminal 63. The frame plate 61 surrounds the vibration plate 41. The frame plate 61 has the external terminal 63 for providing an electrical connection. The connecting portions 62 connect the vibration plate 41 to frame plate 61. The connecting portions 62 have an elasticity of a low spring constant. Thus, the vibration plate 41 is flexibly and elastically supported relative to the frame plate 61 by the two connecting portions 62, that is, at two points.

It should be noted that in the example shown in FIG. 2, there are two connecting portions 62. However, three or more connecting portions 62 may be provided.

The piezoelectric element 42 is provided on the top surface of the vibration plate 41. The reinforcing plate 43 is provided on the bottom surface of the vibration plate 41. The vibration plate 41, the piezoelectric element 42, and the reinforcing plate 43 constitute a piezoelectric actuator 40. The piezoelectric element 42 is made of, for example, PZT ceramics. The vibration plate 41 is made of, for example, stainless steel. The reinforcing plate 43 is made of, for example, stainless steel.

The spacer 53B is provided on the top surface of the frame plate 61. The spacer 53B is made of, for example, resin. The frame plate 61 electrically insulates the vibration plate unit 60 from the electrode conducting plate 70. The electrode conducting plate 70 is provided on the top surface of the spacer 53B. The electrode conducting plate 70 is made of metal. The electrode conducting plate 70 has a frame portion 71, an internal terminal 73, and an external terminal 72. The internal terminal 73 projects inwardly from the frame portion 71. The external terminal 72 projects outwardly from the frame portion 71. An end portion of the internal terminal 73 is joined to the surface of the piezoelectric element 42 with solder. The spacer 53C is provided on the top surface of the electrode conducting plate 70. The spacer 53C is made of, for example, resin. The cover plate 54 is provided on the top surface of the spacer 53C. The cover plate 54 has a discharge hole 55 and a discharge hole 56.

Meanwhile, the spacer 53A is provided on the bottom surface of the vibration plate unit 60. The flexible plate 51 is provided on the bottom surface of the spacer 53A. The flexible plate 51 has a suction hole 52 in the center. The substrate 91 is provided on the bottom surface of the flexible plate 51. The substrate 91 has a cavity 92 in a center portion. The flexible plate 51 has a fixed portion 57 and a movable portion 58. The fixed portion 57 is fixed to the substrate 91. The movable portion 58 is provided inward of the fixed portion 57 and faces the cavity 92. When the piezoelectric actuator 40 vibrates, the movable portion 58 vibrates at substantially the same frequency as the piezoelectric actuator 40.

Thus, when an AC drive voltage is applied to the external terminal 63 and the external terminal 72, the piezoelectric actuator 40 performs concentric flexural vibration. When the piezoelectric actuator 40 vibrates, the movable portion 58 of the flexible plate 51 also vibrates. This enables the piezoelectric pump 10 to cause air to be sucked into the pump chamber 45 through the cavity 92 and the suction hole 52. The piezoelectric pump 10 discharges the air in the pump chamber 45 through the discharge hole 55 and through the discharge hole 56. Here, in the piezoelectric pump 10, virtually, a peripheral portion of the piezoelectric actuator 40 is not fixed. Accordingly, loss due to vibration in the piezoelectric actuator 40 is small, and although the piezoelectric pump 10 is small and has a low profile, high discharge pressure and a high discharge flow rate can be achieved.

Next, the configuration of the valve 101 will be described with reference to FIGS. 1, 3, and 4.

Figure 3:
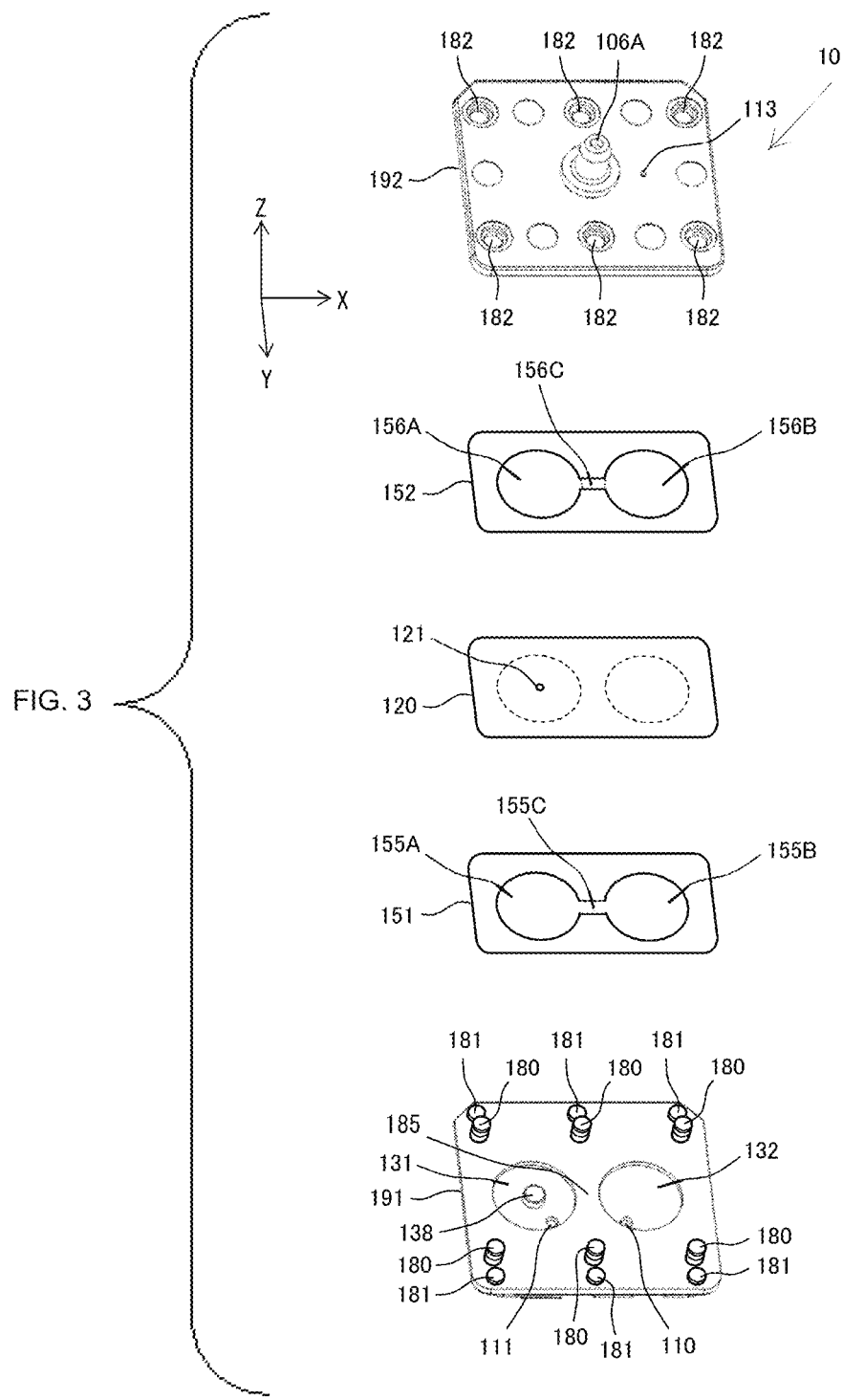
FIG. 3 is an exploded perspective view of a valve 101 shown in FIG. 1.
Figure 4:
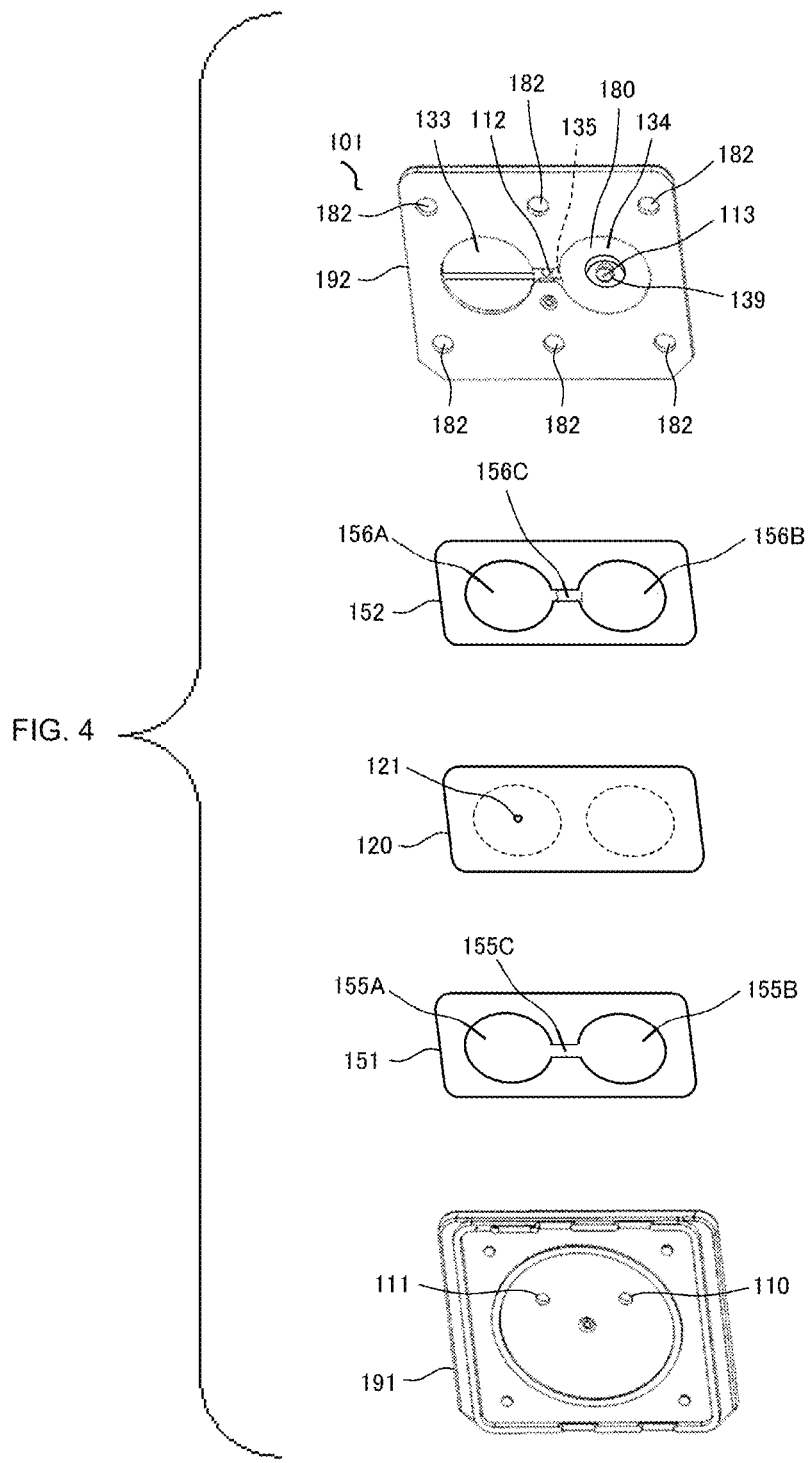
FIG. 4 is an exploded perspective view of the valve 101 shown in FIG. 1.

FIGS. 3 and 4 are exploded perspective views of the valve 101 shown in FIG. 1. FIG. 3 is an exploded perspective view of the valve 101 when viewed from the top surface side on which the cuff 109 is connected to the valve 101. FIG. 4 is an exploded perspective view of the valve 101 when viewed from the bottom surface side on which the piezoelectric pump 10 is joined to the valve 101.

It should be noted that in FIGS. 1, 3, and 4, a Z-axis direction, a Y-axis direction, and an X-axis direction are shown. The Z-axis direction denotes the direction in which the components of the valve 101 are stacked. The X-axis direction denotes the direction in which a check valve 160, a connecting passage 135, and an air-release valve 170 are formed. The Y-axis direction is perpendicular to the Z-axis direction and to the X-axis direction.

As shown in FIGS. 1, 3, and 4, the valve 101 has a first valve housing 191, a first adhesive material 151, a diaphragm 120, a second adhesive material 152, and a second valve housing 192 that are sequentially stacked.

As shown in FIGS. 1, 3, and 4, the second valve housing 192 has a second air hole 112, a third air hole 113, a first valve seat 139, and six depressions 182. The second air hole 112 connects to the internal space of the cuff 109. The third air hole 113 connects to the outside of the fluid controller 100. The first valve seat 139 is formed around the third air hole 113. The second valve housing 192 is made of, for example, resin. The first valve seat 139 is cylindrical and has the third air hole 113 in a center portion.

Together, the second valve housing 192 and the diaphragm 120 form a first flow passage 141. The first flow passage 141 connects the second air hole 112 and the third air hole 113 to each other. The second valve housing 192 has a protruded portion 140. The protruded portion 140 protrudes toward the diaphragm 120 and forms a narrow portion 145 in a portion of the first flow passage 141.

As shown in FIG. 1, the shortest distance z between the protruded portion 140 and the diaphragm 120 in the narrow portion 145 is less than the minimum width of the third air hole 113 in an opening plane. The third air hole 113 is columnar, that is, the minimum width of the third air hole 113 is equal to a diameter 2r of the third air hole 113 in the opening plane.

The protruded portion 140 has a wall surface 144 to which a substance adheres. The wall surface 144 is formed of, for example, a double-sided tape or an adhesive. The wall surface 144 is the side surface of the protruded portion 140 that is not opposite to the diaphragm 120.

As shown in FIG. 1, the top surface of piezoelectric pump 10 is bonded to the bottom surface of the first valve housing 191. As shown in FIGS. 1, 3, and 4, the first valve housing 191 has a first air hole 110, a first air hole 111, a second valve seat 138, and six first protrusions 180. The first air hole 110 connects to the discharge hole 56 in the piezoelectric pump 10. The first air hole 111 connects to the discharge hole 55 in the piezoelectric pump 10. The second valve seat 138 protrudes toward the diaphragm 120. The six first protrusions 180 are opposite to the six depressions 182. The first valve housing 191 further has six second protrusions 181 that are closer than the six first protrusions 180 to the periphery of the first valve housing 191 in a plan view in the Z-axis direction. The first valve housing 191 is made of, for example, resin. The second valve seat 138 is columnar.

The diaphragm 120 is a rectangular thin film. The diaphragm 120 is made of, for example, rubber such as ethylene-propylene-diene-methylene (EPDM) or silicone. As shown in FIGS. 1, 3, and 4, the diaphragm 120 has an opening 121 that is circular in a center portion of a portion opposite to the second valve seat 138. The diameter of the opening 121 is less than that of the second valve seat 138 in the plane in contact with the diaphragm 120.

By fitting the six first protrusions 180 into the six depressions 182, the second valve housing 192 and the first valve housing 191 hold the diaphragm 120 with the second adhesive material 152 and the first adhesive material 151 interposed therebetween. Thus, the diaphragm 120 is fixed to the second valve housing 192 and the first valve housing 191 so that the diaphragm 120 is spaced apart from the first valve seat 139 and so that the periphery of the opening 121 in the diaphragm 120 is in contact with the second valve seat 138, applying pressure to the second valve seat 138.

Together, the diaphragm 120, the first valve housing 191, and the second valve housing 192 form a first valve chamber 131 and a second valve chamber 133. The first valve chamber 131 is annular and connects to the first air hole 111. The second valve chamber 133 is columnar and connects to the second air hole 112 via the connecting passage 135. Together, the diaphragm 120, the first valve housing 191, and the second valve housing 192 form a first valve chamber 132 and a second valve chamber 134. The first valve chamber 132 is columnar and connects to the first air hole 110. The second valve chamber 134 is annular and connects to the second valve chamber 133 via the connecting passage 135.

Together, the diaphragm 120, the second valve housing 192, and the first valve housing 191 also form the check valve 160. Together, the diaphragm 120, the second valve housing 192, and the first valve housing 191 also form the air-release valve 170.

The second adhesive material 152 has second through holes 156A to 156C in a portion facing the second valve chamber 133, the connecting passage 135, and the second valve chamber 134. The second through hole 156A is, for instance, circular and has substantially the same central axis as the second valve chamber 133. The second through hole 156B is, for instance, circular and has substantially the same central axis as the second valve chamber 134. The second adhesive material 152 is, for example, a double-sided tape.

Meanwhile, the first adhesive material 151 has first through holes 155A to 155C in a portion facing the first valve chamber 131 and the first valve chamber 132. The first through hole 155A is, for instance, circular and has substantially the same central axis as the first valve chamber 131. The first through hole 155B is, for instance, circular and has substantially the same central axis as the first valve chamber 132. The first adhesive material 151 is, for example, a double-sided tape.

The first through hole 155A has a smaller diameter than the first valve chamber 131. Similarly, the first through hole 155B has a smaller diameter than the first valve chamber 132. Thus, in the valve 101, a portion of the second adhesive material 152 is present inside the second valve chamber 133 and the second valve chamber 134. Similarly, a portion of the first adhesive material 151 is present inside the first valve chamber 131 and the first valve chamber 132.

The check valve 160 is formed of a portion of the first valve housing 191 having the first air hole 111, a portion of the second valve housing 192 having the second air hole 112, the periphery of the opening 121 in the diaphragm 120, and the second valve seat 138 that protrudes from the first valve housing 191 toward the diaphragm 120. The check valve 160 permits fluid to flow from the first valve chamber 131 toward the second valve chamber 133 and blocks fluid from flowing from the second valve chamber 133 toward the first valve chamber 131.

In the check valve 160, the periphery of the opening 121 in the diaphragm 120 comes into contact with or moves away from the second valve seat 138 in accordance with a magnitude relation between pressure P1 in the first valve chamber 131, pressure P2 in the second valve chamber 133, and applied pressure P3 applied by the periphery of the opening 121 in the diaphragm 120 coming into contact with the second valve seat 138.

The air-release valve 170 is formed of a portion of the first valve housing 191 having the first air hole 110, a portion of the second valve housing 192 having the second air hole 112 and the third air hole 113, a portion of the diaphragm 120, and the first valve seat 139 formed around the third air hole 113.

In the air-release valve 170, an opposite portion 122 of the diaphragm 120 comes into contact with or moves away from the first valve seat 139 in accordance with a magnitude relation between pressure P1 in the first valve chamber 132 and pressure P2 in the second valve chamber 134. The opposite portion 122 of the diaphragm 120 is a portion of the diaphragm 120 that is opposite to the first valve seat 139.

It should be noted that the diaphragm 120 corresponds to an example of the valve body in the present disclosure. The first valve housing 191 and the second valve housing 192 correspond to an example of the valve housing in the present disclosure. The first valve chamber 131 and the first valve chamber 132 correspond to an example of the first valve chamber in the present disclosure. The second valve chamber 133, the connecting passage 135, and the second valve chamber 134 correspond to an example of the second valve chamber in the present disclosure.

Here, as shown in FIG. 1, under conditions of a Young's modulus of the diaphragm 120 of E, a Poisson's ratio of the diaphragm 120 of v, a diameter of a portion of the diaphragm 120 to which the pressure in the first valve chamber 132 is applied of a, a thickness of the diaphragm 120 of t, a distance from the central axis C of the diaphragm 120 to the furthermost peripheral point on the periphery of the third air hole 113 of r, and an amount of expansion at point S in the diaphragm 120 on the axis passing through the peripheral point that is obtained when a pressure difference P is applied of w, the relation of $w=\frac{3}{16}\times((1-v^2)/(E\times t^3))\times P\times(r^2-a^2)^2$ is satisfied (Literature cited: Inoue Tatsuo, *Basics of theory of elasticity*, The Nikkan Kogyo Shimbun, March, 1979).

Here, under conditions of an applied pressure of P3 and a distance from point S in the diaphragm 120 on the axis passing through the peripheral point to the first valve seat 139 of y, the valve 101 satisfies the relation of $y<\frac{3}{16}\times((1-v^2)/(E\times t^3))\times P3\times(r^2-a^2)^2$.

It should be noted that by point S in the diaphragm 120 being brought into contact with the first valve seat 139, the third air hole 113 is completely blocked by the diaphragm 120.

Here, as shown in FIG. 1, in the valve 101, length A by which the second valve seat 138 moves the diaphragm 120 upward is less than length y from point S in the diaphragm 120 on the axis passing through the peripheral point to the first valve seat 139. Thus, the valve 101 satisfies the relation of $y<\frac{3}{16}\times((1-v^2)/(E\times t^3))\times P3\times(r^2-a^2)^2$.

Figure 6:
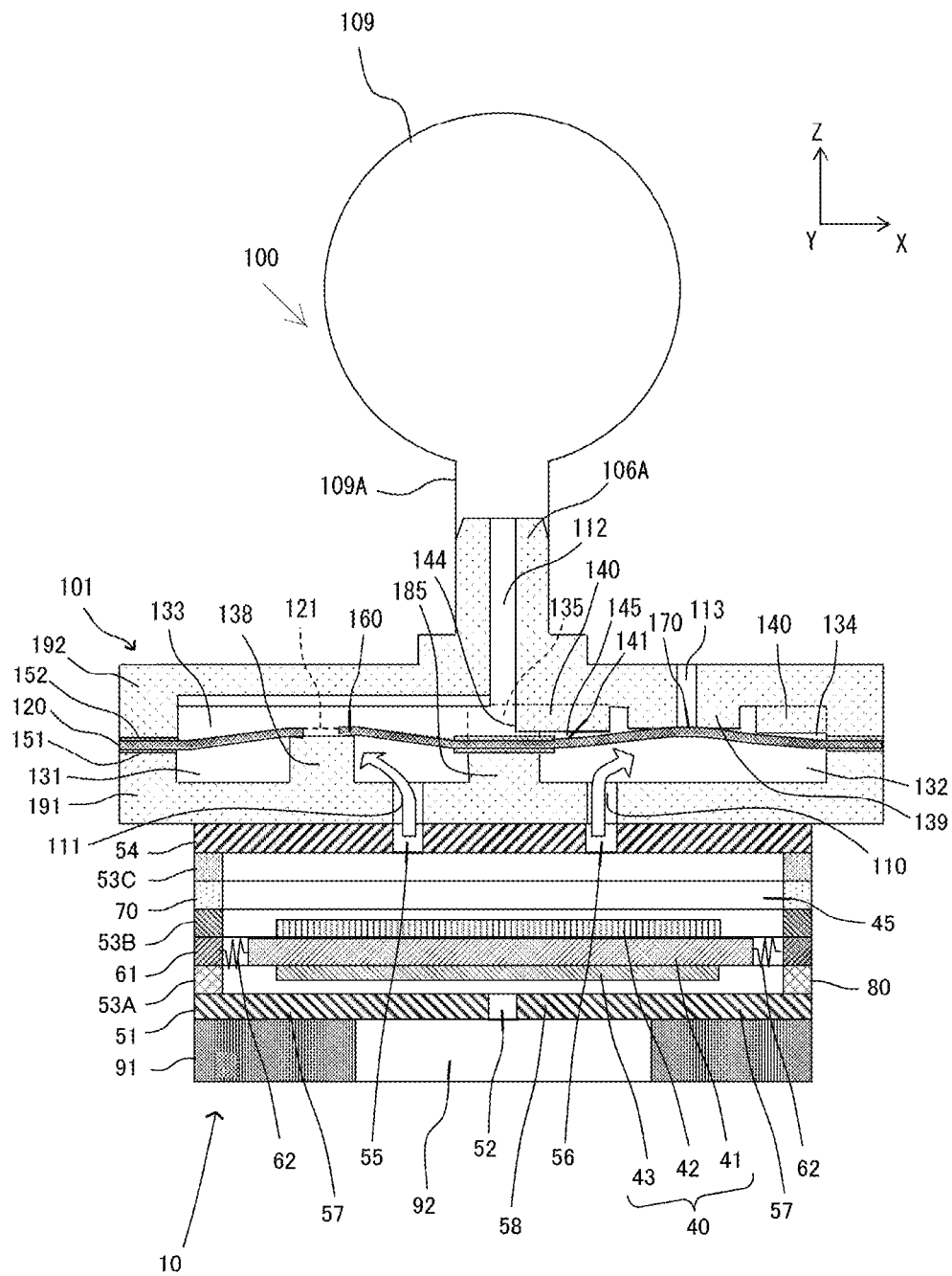
FIG. 6 is a diagram for explaining the flow of the air in the fluid controller 100 immediately after the piezoelectric pump 10 shown in FIG. 1 starts driving.
Figure 7:
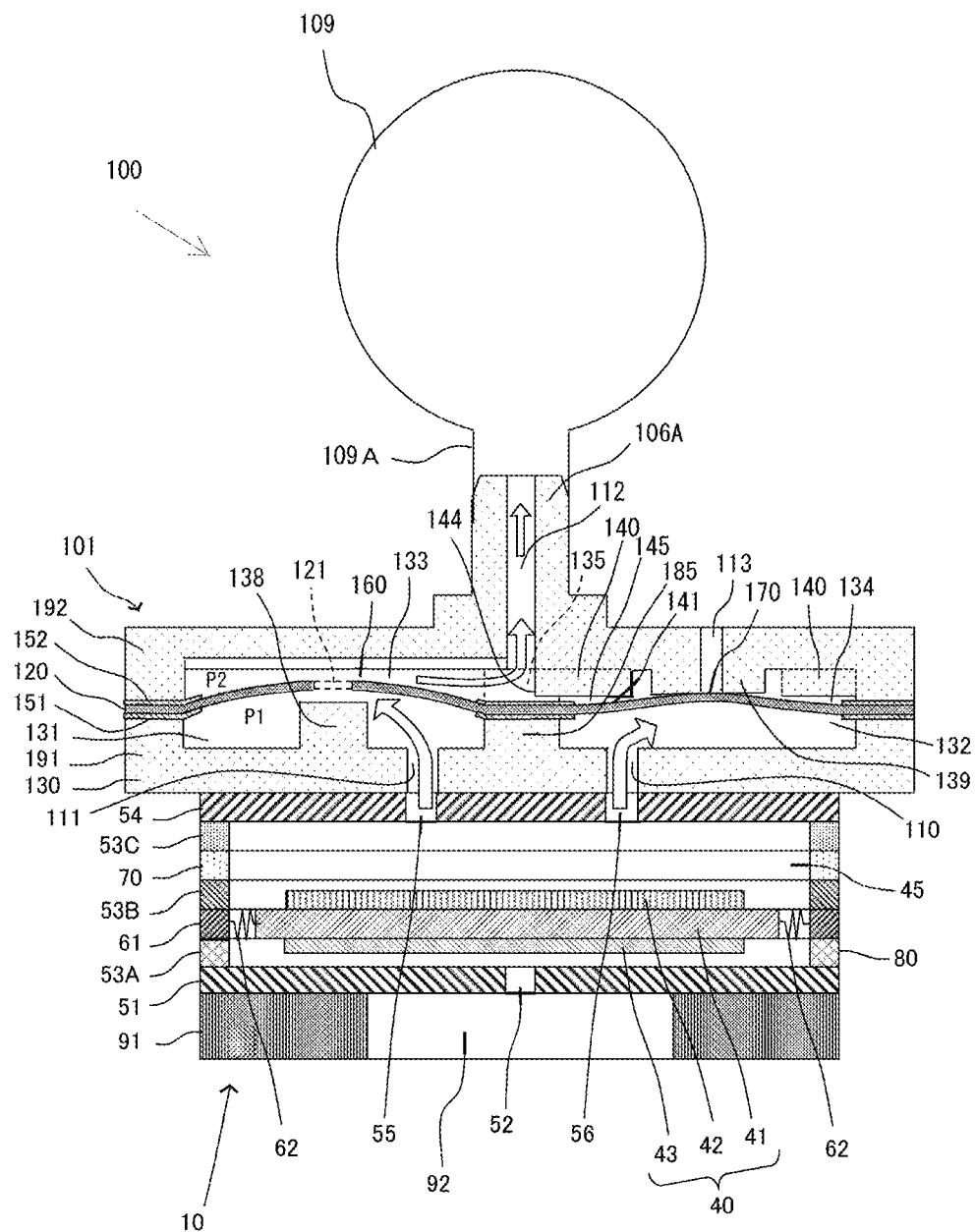
FIG. 7 is a diagram for explaining the flow of the air in the fluid controller 100 during driving of the piezoelectric pump 10 shown in FIG. 1.
Figure 8:
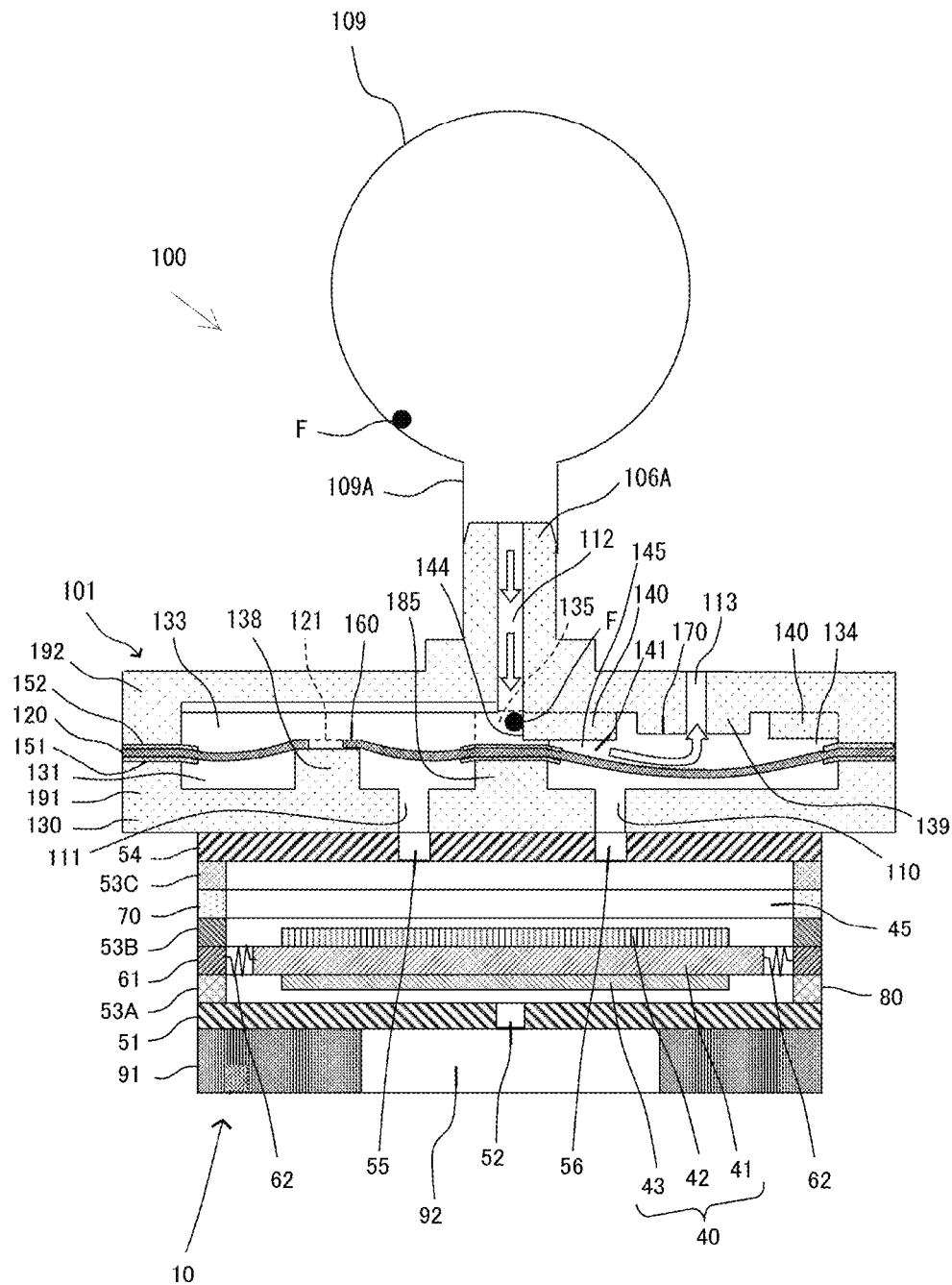
FIG. 8 is a diagram for explaining the flow of the air in fluid controller 100 immediately after the piezoelectric pump 10 shown in FIG. 1 stops driving.

Accordingly, the valve 101 enables the flow of the air shown in FIGS. 6 to 8 when blood pressure is measured.

FIG. 6 is a diagram for explaining the flow of the air in the fluid controller 100 immediately after the piezoelectric pump 10 shown in FIG. 1 starts driving. FIG. 7 is a diagram for explaining the flow of the air in the fluid controller 100 during driving of the piezoelectric pump 10 shown in FIG. 1. FIG. 8 is a diagram for explaining the flow of the air in the fluid controller 100 immediately after the piezoelectric pump 10 shown in FIG. 1 stops driving. The arrows in FIGS. 6, 7, and 8 show the flow of the air.

First, with reference to FIG. 6, the flow of the air in the fluid controller 100 immediately after the piezoelectric pump 10 starts driving will be described.

When starting measuring of blood pressure, the fluid controller 100 drives the piezoelectric pump 10. When the piezoelectric pump 10 is driven, air flows through the cavity 92 and the suction hole 52 into the pump chamber 45 inside the piezoelectric pump 10. The air is then discharged through the discharge hole 55 and through the discharge hole 56 and flows into both the first valve chamber 131 and the first valve chamber 132 in the valve 101.

Thus, in the air-release valve 170, when the pressure P1 in the first valve chamber 132 exceeds the pressure P2 in the second valve chamber 134 and falls below the applied pressure P3, the diaphragm 120 comes into contact with the first valve seat 139, as shown in FIG. 6. Accordingly, in the air-release valve 170, the diaphragm 120 blocks the third air hole 113 to disconnect the third air hole 113 from the second air hole 112. That is, the air-release valve 170 closes.

Next, with reference to FIG. 7, the flow of the air in the fluid controller 100 during driving of the piezoelectric pump 10 will be described.

After the air-release valve 170 closes, and when the pressure P1 in the first valve chamber 132 becomes equal to the applied pressure P3 or greater, in the check valve 160, the periphery of the opening 121 in the diaphragm 120 moves away from the second valve seat 138, as shown in FIG. 7. This connects the first air hole 111 and the second air hole 112 to each other via the opening 121. That is, the check valve 160 opens.

Accordingly, the air is carried from the piezoelectric pump 10 to the cuff 109 through the first air hole 111, the opening 121, and the second air hole 112 in the valve 101 (refer to FIG. 7), thereby increasing the pressure (air pressure) inside the cuff 109.

It should be noted that the diaphragm 120 is fixed to the second valve housing 192 and the first valve housing 191 so that the periphery of the opening 121 in the diaphragm 120 is in contact with the second valve seat 138. The second valve seat 138 applies pressure to the periphery of the opening 121 in the diaphragm 120.

Thus, after flowing through the first air hole 111, the air flows through the opening 121 into the second valve chamber 133 and the second valve chamber 134 with the pressure of the air being slightly lower than the discharge pressure of the piezoelectric pump 10. Meanwhile, the discharge pressure of the piezoelectric pump 10 is applied to the first valve chamber 132.

Accordingly, in the valve 101, the pressure P1 in the first valve chamber 132 slightly exceeds the pressure P2 in the second valve chamber 134, thereby maintaining a state in which the diaphragm 120 blocks the third air hole 113 and a state in which the opening 121 is open.

Next, with reference to FIG. 8, the flow of the air in the fluid controller 100 immediately after the piezoelectric pump 10 stops driving will be described.

When finishing measuring of blood pressure, the fluid controller 100 stops the driving of the piezoelectric pump 10. Here, when the piezoelectric pump 10 stops driving, the air in the pump chamber 45, the air in the first valve chamber 131, and the air in the first valve chamber 132 are rapidly discharged through the suction hole 52 and the cavity 92 in the piezoelectric pump 10 to the outside of the fluid controller 100. The pressure of the cuff 109 is applied to the second valve chamber 133 and the second valve chamber 134 via the second air hole 112.

Thus, in the check valve 160, the pressure P1 in the first valve chamber 132 falls below the pressure P2 in the second valve chamber 134. Accordingly, the diaphragm 120 comes into contact with the second valve seat 138 to block the opening 121.

Also, in the air-release valve 170, the pressure P1 in the first valve chamber 132 falls below the pressure P2 in the second valve chamber 134. Accordingly, the diaphragm 120 moves away from the first valve seat 139, such that the third air hole 113 is no longer blocked.

That is, in the valve 101, the second air hole 112 and the third air hole 113 connect to each other via the connecting passage 135 and the second valve chamber 134. Thus, the air in the cuff 109 is rapidly discharged through the third air hole 113, after flowing through the second air hole 112, the connecting passage 135, and the second valve chamber 134 (refer to FIG. 8). Accordingly, the cuff 109 rapidly deflates, which enables the next measurement of blood pressure to be started immediately.

Here, in the valve 101, the diaphragm 120 is fixed to the second valve housing 192 and the first valve housing 191 so that the diaphragm 120 is spaced apart from the first valve seat 139. Thus, the diaphragm 120 does not block the third air hole 113. That is, the valve 101 maintains a state in which the second air hole 112 and the third air hole 113 connect to each other. Thus, in the valve 101, the air inside the cuff 109 is discharged until the air inside the cuff 109 is at atmospheric pressure.

However, while the fluid controller 100 is charging the compressed air into the cuff 109 and discharging the compressed air from the cuff 109, there is a possibility of foreign matter F being contained in the cuff 109, as shown in FIG. 8. The foreign matter F is, for example, fibers of the cuff 109 that have peeled off from the inner surface of the cuff 109. Fibers on the inner surface of the cuff 109 are more likely to peel off as a result of the fluid controller 100 repeatedly charging the compressed air into the cuff 109 and discharging the compressed air from the cuff 109.

When the compressed air is discharged from the cuff 109, the foreign matter F flows through the second air hole 112 to the connecting passage 135. Here, although the foreign matter F should preferably be discharged through the third air hole 113 to the outside of the fluid controller 100, there is a possibility of, for example, the foreign matter F blocking the opening 121 or the third air hole 113.

Thus, the second valve housing 192 in the valve 101 has a protruded portion 140. Together, the second valve housing 192 and the diaphragm 120 form the first flow passage 141, which connects the second air hole 112 and the third air hole 113 to each other. Together, the protruded portion 140 and the diaphragm 120 form the narrow portion 145 in a portion of the first flow passage 141. The shortest distance z between the protruded portion 140 and the diaphragm 120 in the narrow portion 145 is less than the diameter 2r of the third air hole 113 in the opening plane. Thus, when the compressed air is discharged from the cuff 109, if the width of the foreign matter F that has flowed through the second air hole 112 to the connecting passage 135 is more than the diameter 2r of the third air hole 113 in the opening plane, the foreign matter F cannot pass through a space between the protruded portion 140 and the diaphragm 120. The foreign matter F adheres to the wall surface 144 of the protruded portion 140. As substances stick to the wall surface 144, the foreign matter F is caught on the wall surface 144 of the protruded portion 140.

Moreover, the diameter $2R_1$ of the opening 121 in an opening plane is greater than the diameter $2R_2$ of the second air hole 112 in an opening plane. Thus, when the compressed air is discharged from the cuff 109, it is possible to suppress the foreign matter F that has flowed through the second air hole 112 to the connecting passage 135 from blocking the opening 121.

Accordingly, even if the cuff 109 contains the foreign matter F, the valve 101 can suppress a malfunction due to the foreign matter F from occurring. Particularly, in the air-release valve 170, the valve 101 can suppress the foreign matter F from blocking the third air hole 113 and the opening 121.

It should be noted that when the compressed air is discharged from the cuff 109, if the width of the foreign matter F that has flowed through the second air hole 112 to the connecting passage 135 is less than the diameter 2r of the third air hole 113, and if the foreign matter F passes through the space between the protruded portion 140 and the diaphragm 120, the foreign matter F is discharged through the third air hole 113 to the outside of the second valve housing 192.

As described above, in the valve 101, a portion of the first adhesive material 151 is present inside the first valve chamber 131 and the first valve chamber 132, and a portion of the second adhesive material 152 is present inside the second valve chamber 133 and the second valve chamber 134.

Thus, the second adhesive material 152 and the first adhesive material 151 enable the foreign matter F existent in the first valve chamber 131, the first valve chamber 132, the second valve chamber 133, and the second valve chamber 134 to be caught thereon, as well as enable the second valve housing 192, the first valve housing 191, and the diaphragm 120 to be bonded together.

Effects similar to those provided by the valve 101 can be provided by the fluid controller 100 and a sphygmomanometer each including the valve 101 in this embodiment.

Hereinafter, a fluid controller 200 according to Embodiment 2 of the present disclosure will be described.

Figure 9:
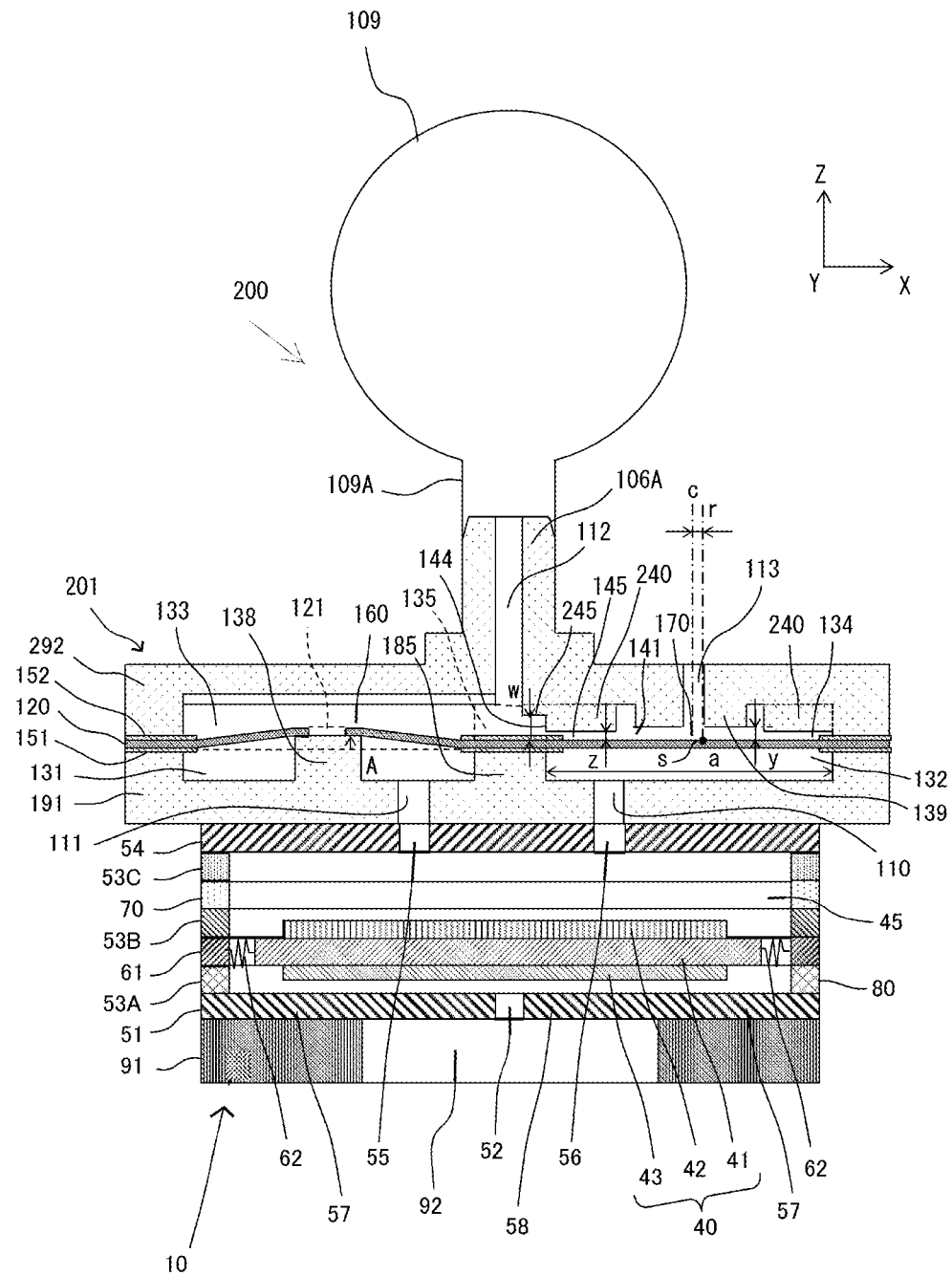
FIG. 9 is a cross-sectional view of the components of a fluid controller 200 according to Embodiment 2 of the present disclosure.
Figure 10:
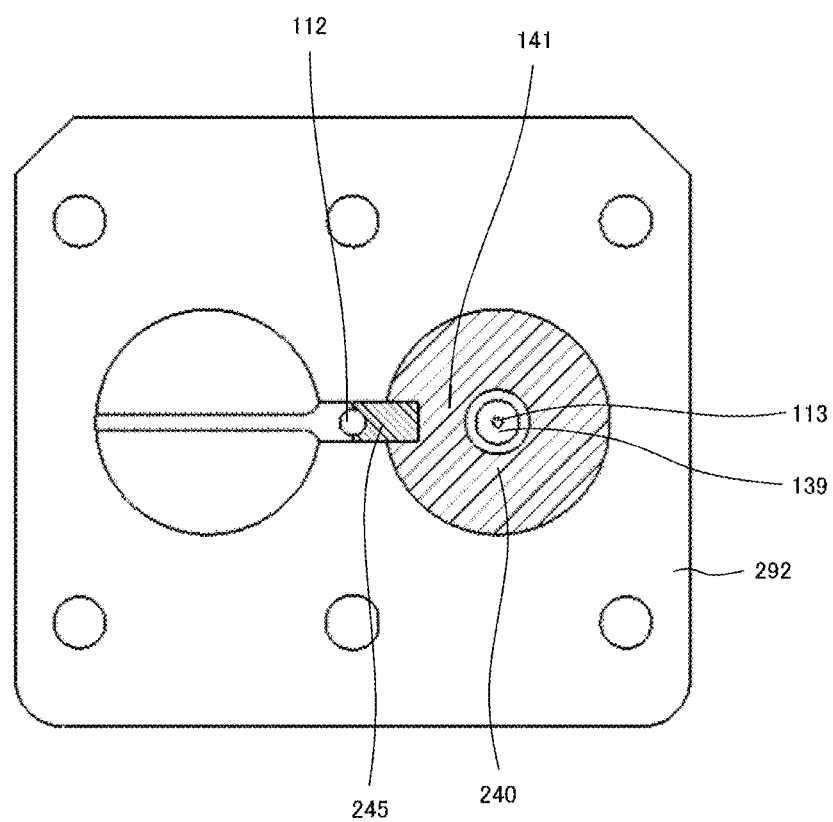
FIG. 10 is a bottom view of a second valve housing 292 shown in FIG. 9.

FIG. 9 is a cross-sectional view of the components of the fluid controller 200 according to Embodiment 2 of the present disclosure. FIG. 10 is a bottom view of a second valve housing 292 shown in FIG. 9.

The fluid controller 200 differs from the fluid controller 100 in terms of the second valve housing 292. The second valve housing 292 in the fluid controller 200 has a protruded portion 240 and an intermediate portion 245. In this respect, the second valve housing 292 in the fluid controller 200 differs from the second valve housing 192 in the fluid controller 100. The protruded portion 240 has a shape different from that of the protruded portion 140. The second valve housing 292 has the intermediate portion 245 between a second air hole 112 and the protruded portion 240. The shortest distance w between the intermediate portion 245 and a diaphragm 120 is greater than the shortest distance z between the protruded portion 240 and the diaphragm 120. The shortest distance z between the protruded portion 240 and the diaphragm 120 is less than a diameter 2r of a third air hole 113. As other configuration is the same as that in Embodiment 1, explanations will be omitted.

Figure 11:
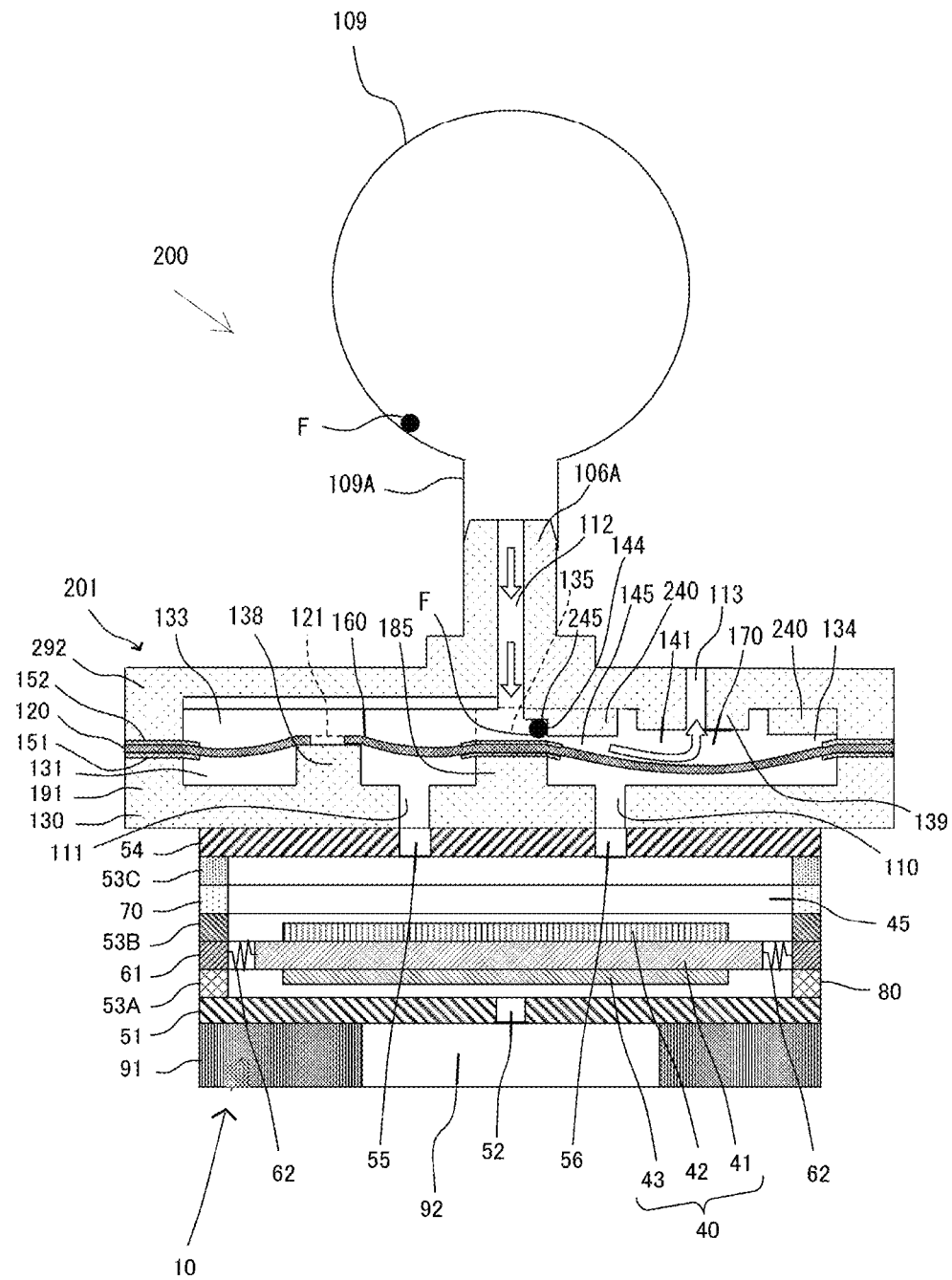
FIG. 11 is a diagram for explaining the flow of the air in the fluid controller 200 immediately after a piezoelectric pump 10 shown in FIG. 9 stops driving.

FIG. 11 is a figure for explaining the flow of the air in the fluid controller 200 immediately after a piezoelectric pump 10 shown in FIG. 9 stops driving. The arrows in FIG. 11 show the flow of the air.

As shown in FIG. 8, in the fluid controller 100, when the compressed air is discharged from the cuff 109, the compressed air that has flowed through the second air hole 112 to the connecting passage 135 potentially flows into the second valve chamber 133. That is, when the foreign matter F that has flowed through the second air hole 112 to the connecting passage 135 flows into the second valve chamber 133, there are a possibility of the foreign matter F getting stuck between the diaphragm 120 and the second valve housing 192 and a possibility of the foreign matter F blocking the opening 121.

Thus, as shown in FIG. 11, in the fluid controller 200, the second valve housing 292 has the intermediate portion 245. Accordingly, since the resistance of a flow passage decreases, when the compressed air is discharged from the cuff 109, the air that has flowed through the second air hole 112 to a connecting passage 135 is more likely to flow toward a second valve chamber 134. That is, foreign matter F that has flowed through the second air hole 112 to the connecting passage 135 is guided to the second valve chamber 134. The foreign matter F that has flowed to the second valve chamber 134 adheres to a wall surface 144 of the protruded portion 240.

Accordingly, a valve 201 can suppress a malfunction due to the foreign matter F from occurring more effectively than the valve 201. Particularly in a check valve 160, the valve 201 can suppress the foreign matter F from getting stuck between the diaphragm 120 and the second valve housing 292 and can suppress the foreign matter F from blocking an opening 121. Effects similar to those provided by the valve 201 can be provided by the fluid controller 200 and a sphygmomanometer each including the valve 201.

Also, since there is the intermediate portion 245, it is possible to avoid that the foreign matter F adhered to the wall surface 144 of the protruded portion 240 from being placed opposite to the opening plane of the second air hole 112. Thus, even if the pieces of foreign matter F adhere to the wall surface 144, it is possible to suppress the pieces of foreign matter F from blocking the second air hole 112.

Hereinafter, a fluid controller 300 according to Embodiment 3 of the present disclosure will be described.

Figure 12:
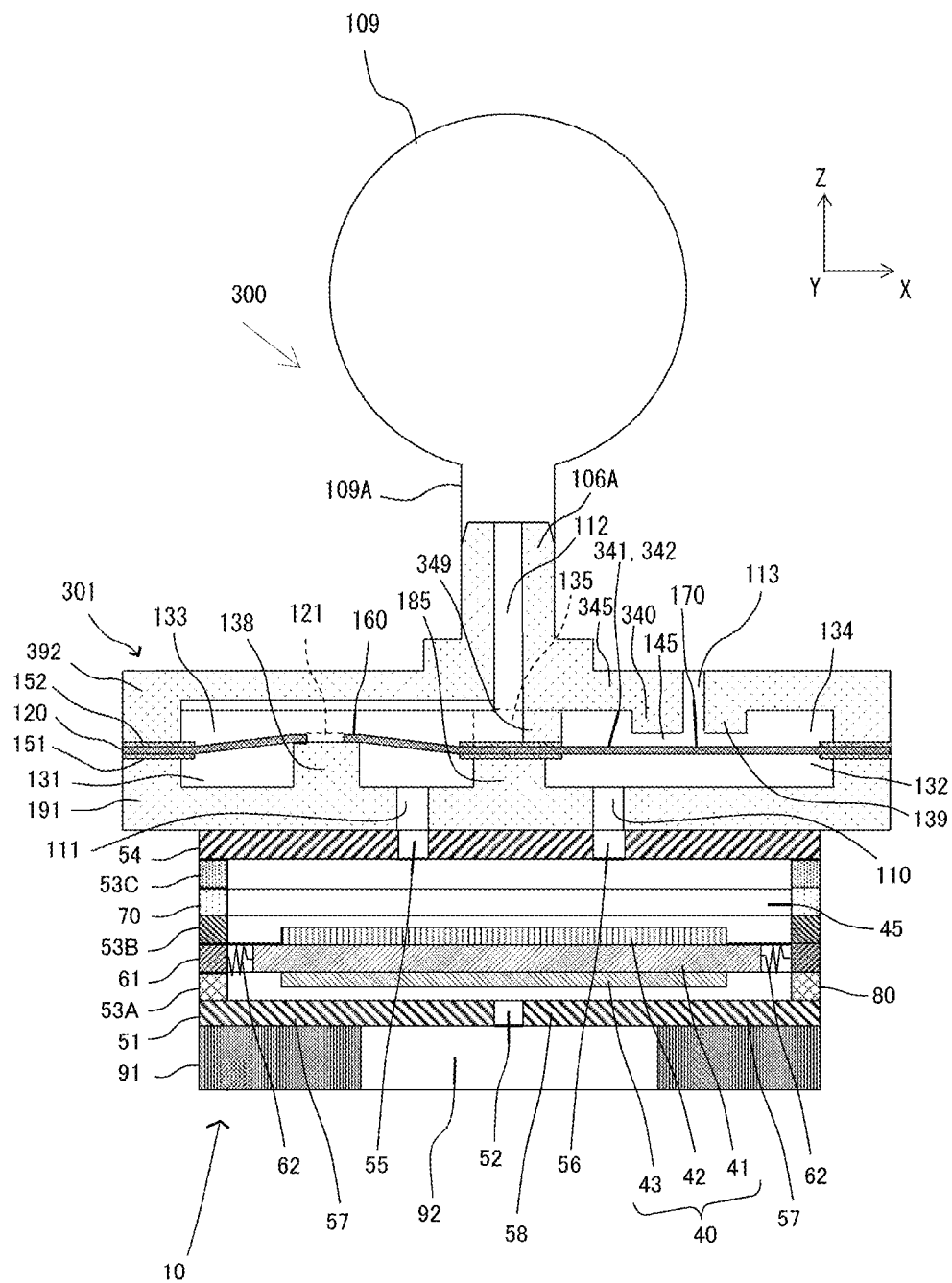
FIG. 12 is a cross-sectional view of the components of a fluid controller 300 according to Embodiment 3 of the present disclosure.
Figure 13:
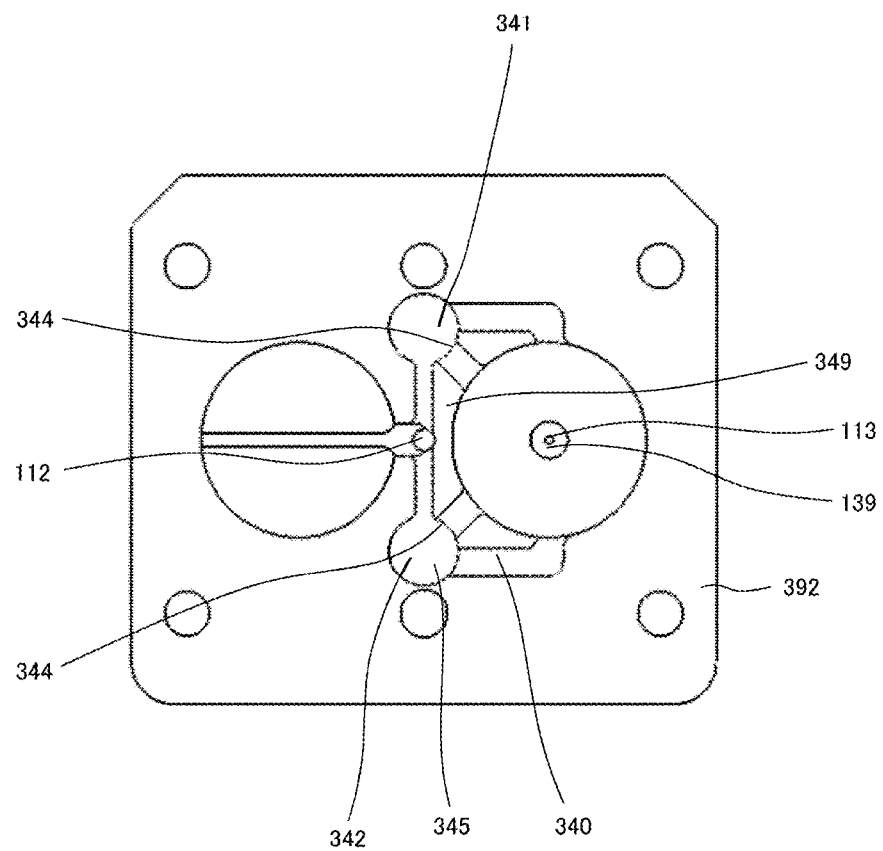
FIG. 13 is a bottom view of a second valve housing 392 shown in FIG. 12.
Figure 14:
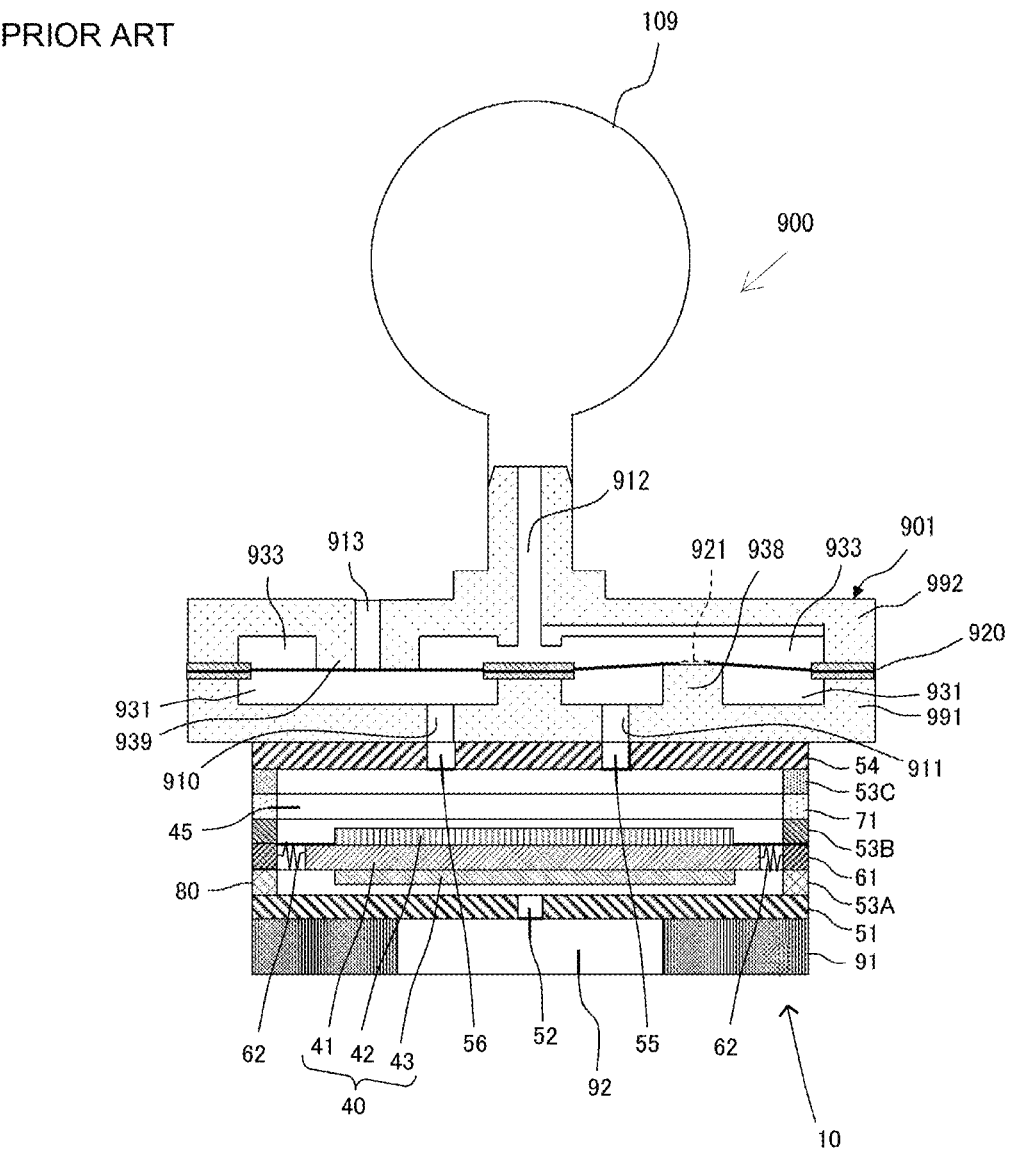
FIG. 14 is a cross-sectional view of the components of a fluid controller 900 according to Patent Document 1.
Figure 15:
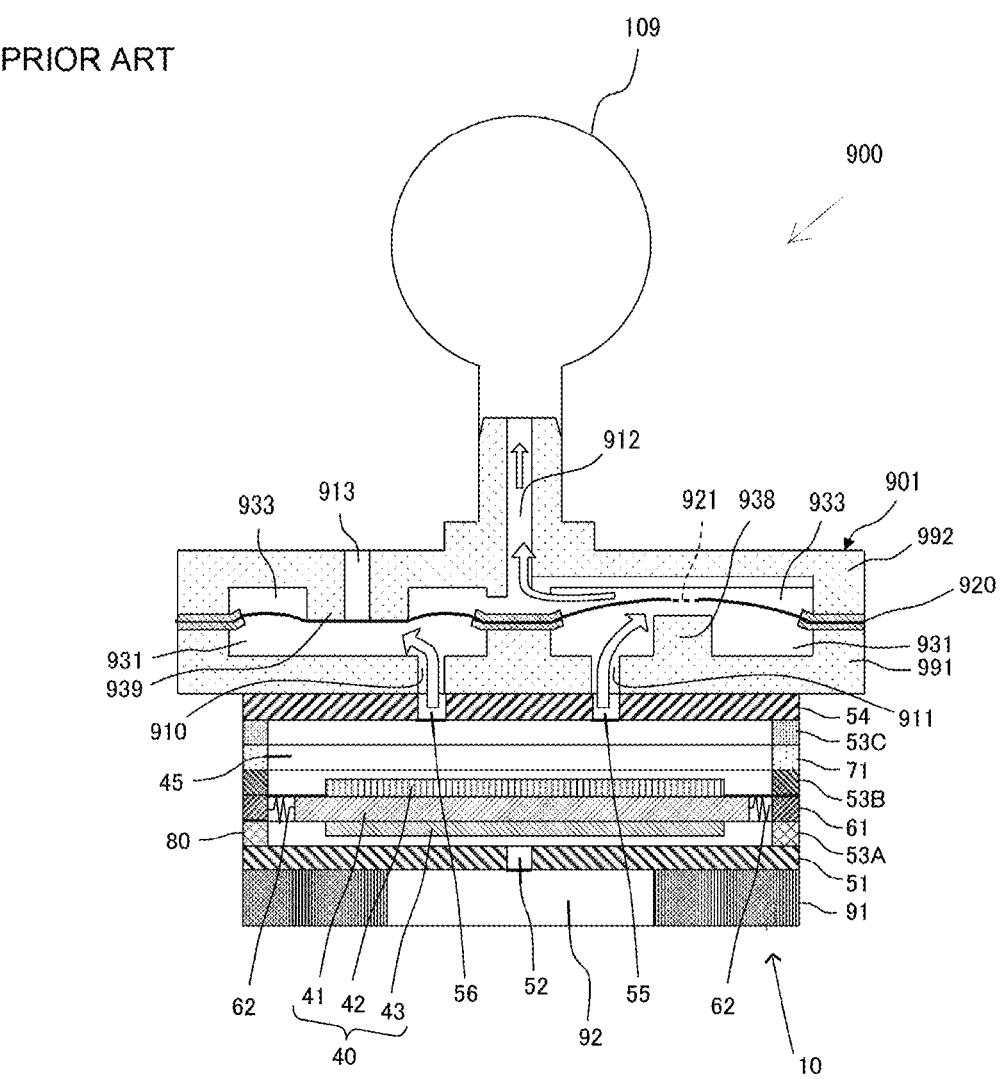
FIG. 15 is a diagram for explaining the flow of the air in the fluid controller 900 during driving of a piezoelectric pump 10 shown in FIG. 14.
Figure 16:
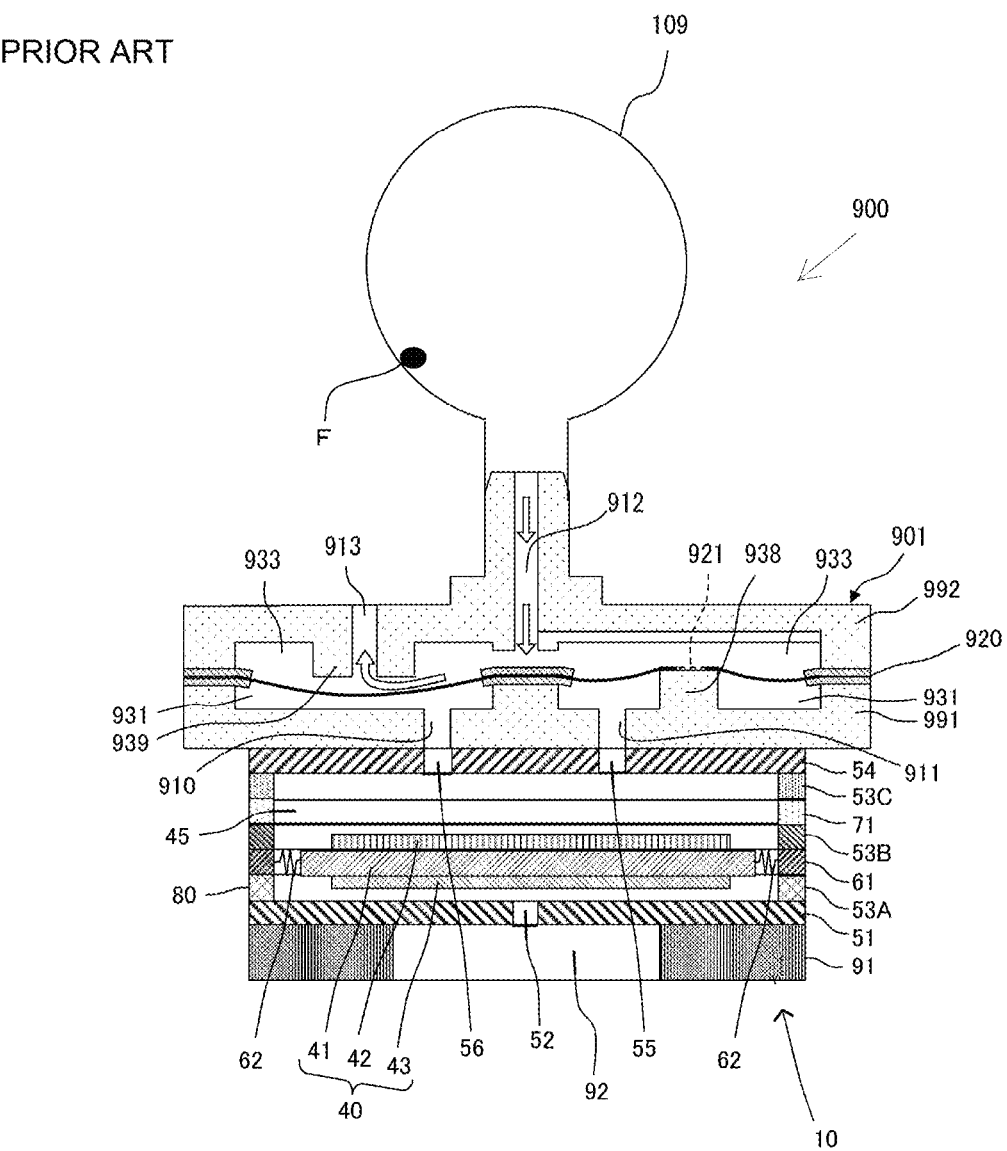
FIG. 16 is a diagram for explaining the flow of the air in the fluid controller 900 immediately after the piezoelectric pump 10 shown in FIG. 14 stops driving.
Figure 17:
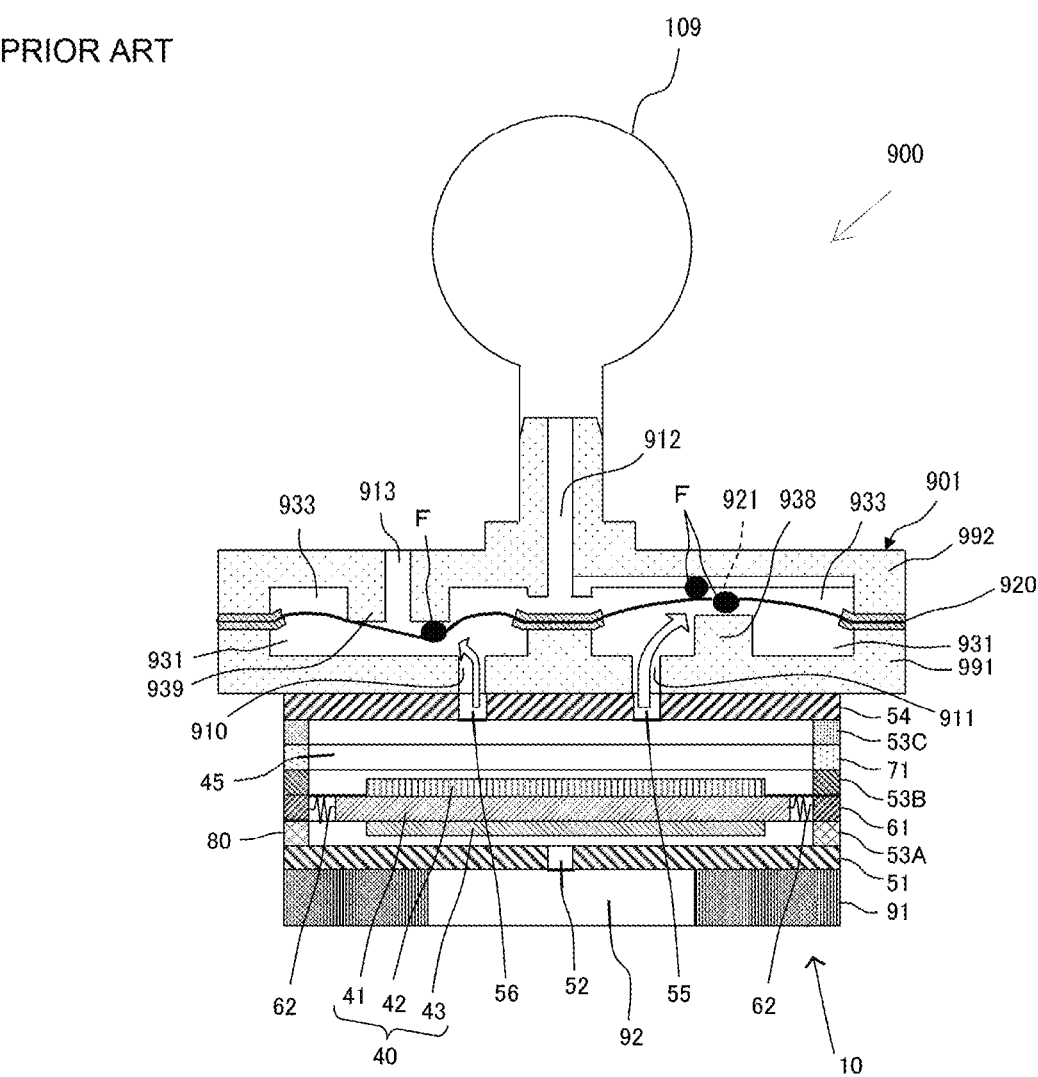
FIG. 17 is a diagram for explaining the flow of the air in the fluid controller 900 during driving of the piezoelectric pump 10 shown in FIG. 14.
Figure 18:
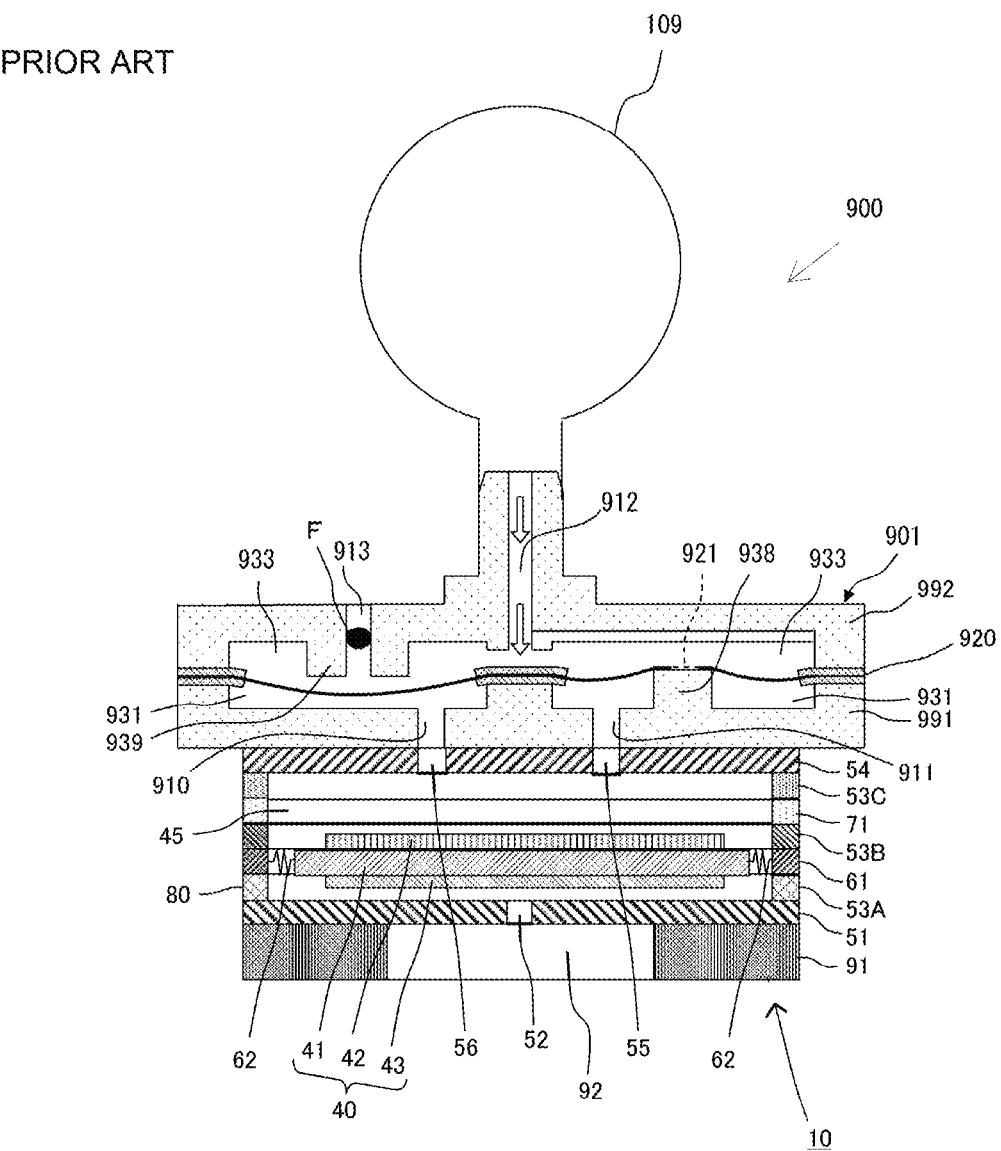
FIG. 18 is a diagram for explaining the flow of the air in the fluid controller 900 immediately after the piezoelectric pump 10 shown in FIG. 14 stops driving.

FIG. 12 is a cross-sectional view of the components of the fluid controller 300 according to Embodiment 3 of the present disclosure. FIG. 13 is a bottom view of a second valve housing 392 shown in FIG. 12.

The fluid controller 300 differs from the fluid controller 200 in terms of the second valve housing 392. Together, the second valve housing 392 and a diaphragm 120 form a first flow passage 341 and a second flow passage 342. In this respect, the second valve housing 392 in the fluid controller 300 differs from the second valve housing 292 in the fluid controller 200. The second valve housing 392 has a protruded portion 340, an intermediate portion 345, and a barrier 349 between a second air hole 112 and a third air hole 113. The protruded portion 340 has a shape different from that of the protruded portion 240. The second valve housing 392 has the intermediate portion 345 between the second air hole 112 and the protruded portion 340. The shortest distance between the intermediate portion 345 and a diaphragm 120 is greater than the shortest distance between the protruded portion 340 and the diaphragm 120. The shortest distance between the protruded portion 340 and the diaphragm 120 is less than a diameter 2r of the third air hole 113 in an opening plane. As other configuration is the same as that in Embodiment 1 and 2, explanations will be omitted.

Figure 5:
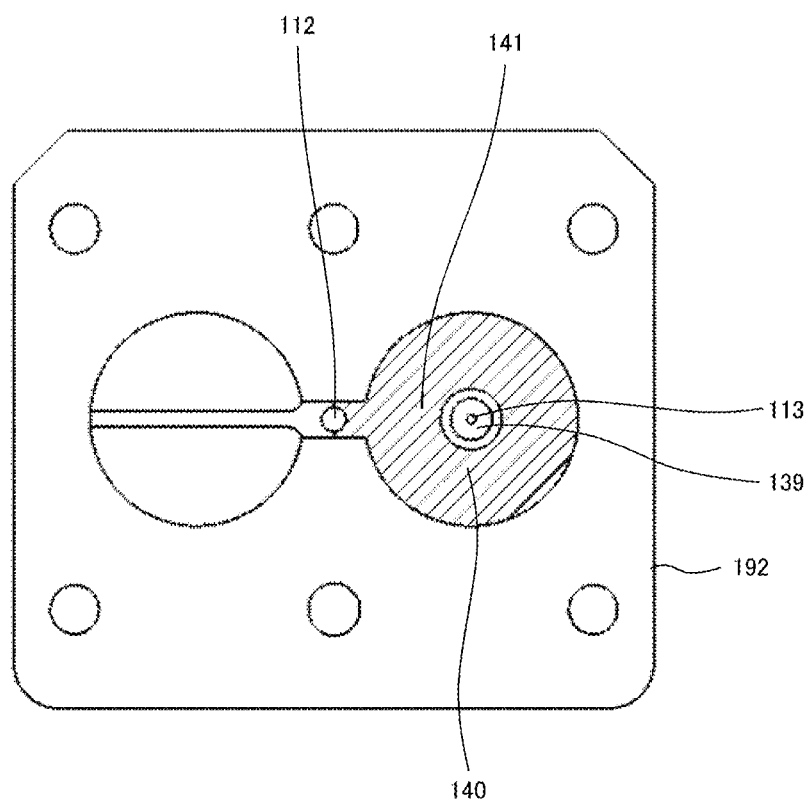
FIG. 5 is a bottom view of a second valve housing 192 shown in FIG. 1.

As shown in FIG. 13, the first flow passage 341 connects the second air hole 112 and the third air hole 113 to each other by making a detour around the barrier 349. Thus, the first flow passage 341 is longer than the shortest distance between the second air hole 112 and the third air hole 113. That is, the first flow passage 341 is longer than the first flow passages 141 shown in FIGS. 5 and 10.

Similarly, as shown in FIG. 13, the second flow passage 342 connects the second air hole 112 and the third air hole 113 to each other by making a detour around the barrier 349. Thus, the second flow passage 342 is longer than the shortest distance between the second air hole 112 and the third air hole 113. That is, the second flow passage 342 is longer than the first flow passages 141 shown in FIGS. 5 and 10.

As such, even if foreign matter F blocks either the first flow passage 341 or the second flow passage 342, when the compressed air is discharged from a cuff 109, the valve 301 can discharge air that has flowed through the second air hole 112 to a connecting passage 135, through the first flow passage 341 or the second flow passage 342 that is not blocked and then through the third air hole 113.

Moreover, the first flow passage 341 and the second flow passage 342 are longer than the first flow passage 141, thereby increasing the possibility of the foreign matter F being caught thereon.

Accordingly, a valve 301 can suppress a malfunction due to the foreign matter F from occurring more effectively than the valve 201. Effects similar to those provided by the valve 301 can be provided by the fluid controller 300 and a sphygmomanometer each including the valve 301.

Other Embodiment

It should be noted that although air is used as fluid in Embodiments 1 to 3, this is just an example, and a gas other than air may be used.

Moreover, the fluid controller 100, the fluid controller 200, and the fluid controller 300 charge air into the cuffs 109 in Embodiments 1 to 3. However, this is just an example. Upon implementation, the fluid controllers may charge gas into containers other than the cuffs.

As shown in FIGS. 1, 9, and 12, in Embodiments 1 to 3, the fluid controller 100, the fluid controller 200, and the fluid controller 300 each include the barrier 185 that separates the first valve chamber 131 from the first valve chamber 132. However, this is just an example. Upon implementation, the barriers 185 may be removed from the fluid controller 100, the fluid controller 200, and the fluid controller 300, and the first valve chamber 131 and the first valve chamber 132 may connect to each other in each fluid controller. In this instance, the first valve housing 191 may include either the first air hole 110 or the first air hole 111. Also, in this instance, the piezoelectric pump 10 may include either the discharge hole 55 or the discharge hole 56.

The piezoelectric pumps 10 in Embodiments 1 to 3 include the piezoelectric actuators 40 that are unimorph piezoelectric actuators and that perform flexural vibration. However, the piezoelectric pumps 10 may include bimorph piezoelectric actuators that perform flexural vibration. Here, in the bimorph piezoelectric actuator, the piezoelectric element 42 is attached to each side of the vibration plate 41.

The piezoelectric elements 42 in Embodiments 1 to 3 are made of PZT ceramics. However, this is just an example. For instance, the piezoelectric elements 42 may be made of a piezoelectric material such as non-zinc piezoelectric ceramics including, for example, potassium-sodium niobate ceramics and alkali niobate ceramics.

In Embodiments 1 to 3, the fluid controller 100, the fluid controller 200, and the fluid controller 300 each include the piezoelectric pump 10 driven by the piezoelectric element 42 expanding and contracting. However, this is just an example. The fluid controllers may include, for example, electromagnetic pumps driven by electromagnetic induction.

As the third air holes 113 are columnar in Embodiments 1 to 3, the minimum width of the third air hole 113 corresponds to the diameter 2r of the third air hole 113. However, this is just an example. If the third air holes have other shapes (such as the shape of a square pole), the shortest distance between the protruded portion and the valve body should be less than the minimum width of the third air hole.

The explanations in Embodiments 1 to 3 are mere exemplifications in all aspects, and the present disclosure is not limited to these exemplifications. The scope of the present disclosure is not defined by the embodiments above but is defined by the scope of claims for a patent. Furthermore, the scope of the present disclosure covers the scope of claims for a patent and the scope of equivalents.

F foreign matter
10 piezoelectric pump
40 piezoelectric actuator
41 vibration plate
42 piezoelectric element
43 reinforcing plate
45 pump chamber
51 flexible plate
52 suction hole
53A, 53B, 53C spacer
54 cover plate
55, 56 discharge hole
57 fixed portion
58 movable portion
60 vibration plate unit
61 frame plate
62 connecting portion
63, 72 external terminal
70 electrode conducting plate
71 frame portion
73 internal terminal
80 pump housing
91 substrate
92 cavity
100, 200, 300 fluid controller
101, 201, 301 valve
106A nozzle
109 cuff
109A cuff rubber band
110, 111 first air hole
112 second air hole
113 third air hole
120 diaphragm
121 opening
122 opposite portion
131, 132 first valve chamber
133, 134 second valve chamber
135 connecting passage
138 second valve seat
139 first valve seat
140, 240, 340 protruded portion
141 first flow passage 144 wall surface
145 narrow portion
151 first adhesive material
152 second adhesive material
155A, 155B first through hole
156A, 156B second through hole
160 check valve
170 air-release valve
180 first protrusion
181 second protrusion
182 depression
185 barrier
191 first valve housing
192, 292, 392 second valve housing
245, 345 intermediate portion
341 first flow passage
342 second flow passage
349 barrier
900 flow controller
901 valve
910, 911 first air hole
912 second air hole
913 third air hole
920 diaphragm
921 opening
931 first valve chamber
933 second valve chamber
938, 939 valve seat
991 first valve housing
992 second valve housing

The invention claimed is:

1. A valve comprising:
a valve housing including a first air hole, a second air hole, and a third air hole, the first air hole connecting to an outside of the valve housing and being an air hole into which a fluid flows, the second air hole connecting to a container into which the fluid flows or the second air hole being from which the fluid flows, the third air hole connecting to the outside of the valve housing to which the fluid flows out; and
a valve body providing a first flow passage together with the valve housing, the first flow passage connecting the second air hole and the third air hole to each other, wherein:
when the valve body comes into contact with the valve housing, an inside of the valve housing is not in fluid communication with the outside of the valve housing via the third air hole, and when the valve body moves away from the valve housing, the inside of the valve housing is in fluid communication with the outside of the valve housing via the third air hole,
the valve housing has a protruded portion protruding toward the valve body and providing a portion of the first flow passage,
the first flow passage has a narrow portion provided by the protruded portion and the valve body, and
a shortest distance between the protruded portion and the valve body is less than a minimum width of the third air hole in an opening plane.

2. The valve according to claim 1, wherein:
the valve housing further includes a first valve seat,
the first valve seat is provided around the third air hole, and
when the valve body comes into contact with the first valve seat, an inside of the valve housing is not in fluid communication with the outside of the valve housing via the third air hole, and when the valve body moves away from the first valve seat, the inside of the valve housing is in fluid communication with the outside of the valve housing via the third air hole.

3. The valve according to claim 2, wherein:
together, the valve body and the valve housing provide a first valve chamber and a second valve chamber, the first valve chamber connecting to the first air hole, and the second valve chamber connecting to the second air hole and the third air hole,
the valve housing further includes a second valve seat to which the valve body is able to come into contact with or move away from,
the valve body has an opening allowing the first valve chamber and the second valve chamber to connect to each other, and
when the valve body comes into contact with the second valve seat, the first valve chamber and the second valve chamber are not in fluid communication with each other via the opening, and when the valve body moves away from the second valve seat, the first valve chamber and the second valve chamber are in fluid communication with each other via the opening.

4. The valve according to claim 3, wherein a maximum width of the opening in an opening plane is more than a maximum width of the second air hole in an opening plane.

5. The valve according to claim 1, wherein:
the valve housing has an intermediate portion between the second air hole and the protruded portion, and
a shortest distance between the intermediate portion and the valve body is greater than a shortest distance between the protruded portion and the valve body in the narrow portion.

6. The valve according to claim 1, wherein the first flow passage is longer than a shortest distance between the second air hole and the third air hole.

7. The valve according to claim 1, wherein together, the valve housing and the valve body provide a second flow passage, the second flow passage differing from the first flow passage and providing fluid communication between the second air hole and the third air hole.

8. The valve according to claim 1, wherein:
the protruded portion has a wall surface configured to adhere to a substance, and
the wall surface is not opposite to the valve body.

9. The valve according to claim 3,
wherein when a first pressure in the first valve chamber exceeds a second pressure in the second valve chamber, the valve body is configured to move away from the second valve seat to provide fluid communication between the first air hole and the second air hole via the opening, and the valve body is configured to come into contact with the first valve seat to block the third air hole, and
when the first pressure in the first valve chamber becomes equal to or less than the second pressure in the second valve chamber, the valve body is configured to move away from the first valve seat to provide fluid communication between the second air hole and the third air hole via the first flow passage, and the valve body is configured to come into contact with the second valve seat to block the opening.

10. A fluid controller comprising:
a pump having a discharge hole;
the valve according to claim 1; and
a container for storing gas,
wherein the first air hole in the valve is in fluid communication with the discharge hole in the pump, the second air hole in the valve is in fluid communication with the container, and the third air hole in the valve is in fluid communication with the atmosphere.

11. A sphygmomanometer comprising the fluid controller according to claim 9.

12. The valve according to claim 1, wherein a thickness of the first flow passage is less than a longitudinal distance of the first flow passage.

13. The valve according to claim 2, wherein a thickness of the first flow passage is less than a longitudinal distance of the first flow passage.

14. The valve according to claim 3, wherein a thickness of the first flow passage is less than a longitudinal distance of the first flow passage.

15. The valve according to claim 2, wherein:

the valve housing has an intermediate portion between the second air hole and the protruded portion, and a shortest distance between the intermediate portion and the valve body is greater than a shortest distance between the protruded portion and the valve body in the narrow portion.

16. The valve according to claim 3, wherein:

the valve housing has an intermediate portion between the second air hole and the protruded portion, and a shortest distance between the intermediate portion and the valve body is greater than a shortest distance between the protruded portion and the valve body in the narrow portion.

17. The valve according to claim 2, wherein the first flow passage is longer than a shortest distance between the second air hole and the third air hole.

18. The valve according to claim 3, wherein the first flow passage is longer than a shortest distance between the second air hole and the third air hole.

19. The valve according to claim 2, wherein together, the valve housing and the valve body provide a second flow passage, the second flow passage differing from the first flow passage and providing fluid communication between the second air hole and the third air hole.

20. The valve according to claim 3, wherein together, the valve housing and the valve body provide a second flow passage, the second flow passage differing from the first flow passage and providing fluid communication between the second air hole and the third air hole.

* * * * *